US008101360B2

(12) United States Patent
Kornman et al.

(10) Patent No.: US 8,101,360 B2
(45) Date of Patent: Jan. 24, 2012

(54) IL-1 GENE CLUSTER, INSULIN RESISTANCE AND CORONARY ARTERY DISEASE ASSOCIATED POLYMORPHISMS AND HAPLOTYPES AND METHODS OF USING SAME

(75) Inventors: Kenneth S. Kornman, Newton, MA (US); Kenneth Huttner, Chestnut Hill, MA (US)

(73) Assignee: Interleukin Genetics, Inc., Waltham, MA (US)

( * ) Notice: Subject to any disclaimer, the term of this patent is extended or adjusted under 35 U.S.C. 154(b) by 566 days.

(21) Appl. No.: 11/985,614

(22) Filed: Nov. 15, 2007

(65) Prior Publication Data
US 2009/0098141 A1  Apr. 16, 2009

Related U.S. Application Data

(60) Provisional application No. 60/865,988, filed on Nov. 15, 2006.

(51) Int. Cl.
  *C12Q 1/68* (2006.01)
  *C12P 19/34* (2006.01)
  *C07H 21/04* (2006.01)

(52) U.S. Cl. ............... 435/6.11; 435/91.2; 536/23.5; 536/24.31; 536/24.33

(58) Field of Classification Search ............ None
See application file for complete search history.

(56) References Cited

U.S. PATENT DOCUMENTS

| | | | |
|---|---|---|---|
| 4,968,607 A | 11/1990 | Dower et al. | 435/69.1 |
| 5,686,246 A | 11/1997 | Kornman et al. | 435/6 |
| 6,140,047 A | 10/2000 | Duff et al. | 435/6 |
| 6,210,877 B1 | 4/2001 | Francis et al. | 435/6 |
| 6,268,142 B1 | 7/2001 | Duff et al. | 435/6 |
| 6,524,795 B1 | 2/2003 | Francis et al. | 435/6 |
| 6,558,905 B1 | 5/2003 | Van Dijk et al. | 435/6 |
| 6,706,478 B2 | 3/2004 | Duff et al. | 435/6 |
| 6,730,476 B1 | 5/2004 | Duff et al. | 435/6 |
| 6,733,967 B1 | 5/2004 | Kornman et al. | 435/6 |
| 6,746,839 B1 | 6/2004 | Duff et al. | 435/6 |
| 2002/0182612 A1 | 12/2002 | Duff et al. | 435/6 |
| 2003/0235890 A1 | 12/2003 | Wyllie et al. | 435/69.52 |
| 2004/0171038 A1 | 9/2004 | Nicklin et al. | 435/6 |
| 2005/0064453 A1 | 3/2005 | Duff et al. | 435/6 |
| 2005/0084882 A1 | 4/2005 | Kornman et al. | 435/6 |
| 2005/0282198 A1 | 12/2005 | Duff et al. | 435/6 |
| 2006/0252055 A1 | 11/2006 | Francis et al. | 435/6 |
| 2007/0264645 A1 | 11/2007 | Kornman et al. | 435/6 |
| 2008/0254476 A1 | 10/2008 | Kornman et al. | 435/6 |
| 2008/0254477 A1 | 10/2008 | Kornman et al. | 435/6 |
| 2008/0254478 A1 | 10/2008 | Kornman et al. | 435/6 |

FOREIGN PATENT DOCUMENTS

| | | |
|---|---|---|
| WO | WO 98/40517 | 9/1998 |
| WO | WO 00/72015 | 11/2000 |
| WO | WO 02/103031 | 12/2002 |
| WO | WO 03/044176 | 5/2003 |
| WO | WO 03/064600 | 8/2003 |
| WO | WO 03/106652 | 12/2003 |
| WO | WO 2005/108619 | 11/2005 |
| WO | WO 2007/050794 | 5/2007 |
| WO | WO 2008/060627 | 5/2008 |

OTHER PUBLICATIONS

Lucentini , The Scientist. Dec. 2004, p. 20.*
Hirschhorn et al. Genetics in Medicine. 2002.4(2): 45-61.*
Halushka Nature. Jul. 1999.22: 239-247.*
Gonzalez et al, Cytokine, 1995, vol. 7, p. 631, abstract A224.*
Puertollano et al, (American Journal of Medical Genetics, (Neuropsychiatric Genetics), vol. 74, 1997, pp. 342-344.*
U.S. Appl. No. 09/617,720, filed Jul. 17, 2000, Nicklin et al.
Armitage et al. (2000), Journal of Periodontology 71:164-171.
Bailly et al. (1993), Eur. J. Immunol. 23:1240-1245.
Clay et al., (1996), Hum Genet. 97:723-726.
Francis et al. (1999), Circulation 99:861-866.
Guzman et al. (2003), Journal of Periodontology 74:1183-1190.
Halushka et al. (1999), Nature 22:239-247.
Hermann et al. (2005), European Cytokine Network 16:277-281.
Hirschhorn et al. (2002), Genetics in Medicine 4:45-61.
Kornman et al. (1999) Journal of Periodontal Research 34:353-357.
Langdahl et al. (2000), Journal of Bone and Mineral Research 15:402-414.
Latkovskis et al. (2004), European Journal of Immunogenetics 31:207-213.
Lucentini et al. (2004), The Scientist p. 20.
Mansfield et al. (1994), Gastroenterology 106:637-642.
Minton et al. (2005), Human Immunology 66:127-132.
Muraki et al. (2004), The Journal of Rheumatology 31:720-725.
Murphy et al. (2001), Neurology 56:1595-1597.
Nicklin et al. (1994), Genomics 19:382-384.
Rosenmann et al. (2004), Neuroscience Letters 363:131-133.
Zmuda et al. (2006), Journal Musculoskelet Neuronal Interaction 6:3-15.
International Search Report for PCT/US2007/024107 mailed Aug. 12, 2008.
International Search Report for PCT/US2006/041847 mailed Aug. 28, 2007.
International Search Report for PCT/US2003/02232 mailed Sep. 14, 2005.

* cited by examiner

*Primary Examiner* — Bridget E Bunner
*Assistant Examiner* — Fozia Hamud
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The invention provides methods and compositions relating to identification and use of genetic information from the IL-1 gene cluster—including the structure and organization of novel IL-1-like genes found within the IL-1 locus as well as polymorphisms and associated haplotypes within these genes. The invention thereby expands the repertoire of useful genetic information available from the IL-1 locus—which contains the previously-identified IL-1α, IL-1β and IL-1RN genes, for predicting IL-1 associated phenotypes (e.g. increased or decreased risks of insulin resistance associated pathologies) and for treating IL-1 haplotype associated insulin resistance associated pathologies.

9 Claims, 1 Drawing Sheet

SEQUENCE LISTING

```
<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggttttag aaatcatcaa gcctagggca                                            30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aatgaaagga ggggaggatg acagaaatgt                                            30

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tggcattgat ctggttcatc                                                       20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtttaggaat cttcccactt                                                       20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcaggtgtc ctcgaagaaa tcaaa                                                 25
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6 gctttttgc tgtgagtccc g                                              21

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctatctgagg aacaaccaac tagtagc                                       27

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taggacattg cacctagggt ttgt                                          24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acatcaggga aaagccattg                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgggaatggg cactatgatt                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaatcagaag gctgcttgga                                               20

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgggtgaat gggaatttga                                                   20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcacagaggc tcactccctt g                                                 21

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gattggggac atgcagagtc caagg                                             25
```

IL-1 GENE CLUSTER, INSULIN RESISTANCE AND CORONARY ARTERY DISEASE ASSOCIATED POLYMORPHISMS AND HAPLOTYPES AND METHODS OF USING SAME

CROSS-REFERENCE TO RELATED APPLICATIONS

This application claims priority from U.S. Provisional Application Ser. No. 60/865,988 filed on Nov. 15, 2006, the disclosure of which are incorporated herein by reference in their entireties.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

FIELD OF THE INVENTION

The present invention relates in part to methods and compositions relating to identification and use of genetic information from the IL-1 gene cluster—including the structure and organization of novel IL-1-like genes found within the IL-1 locus as well as polymorphisms and associated haplotypes within these genes.

BACKGROUND OF THE INVENTION

IL-1 is a primary inflammatory cytokine and has been implicated in mediating both acute and chronic pathological inflammatory diseases. Two functionally similar molecules, IL-1α and IL-1β, are encoded by separate genes (respectively, IL1A and IL1B). The third gene of the family (IL1RN) encodes IL-1 receptor antagonist (IL-1ra), an anti-inflammatory non-signaling molecule that competes for receptor binding with IL-1α and IL-1β. Pairwise comparison of IL-1α, IL-1β and IL-1ra yields <25% identity in each case, yet X-ray crystallography of IL-1β and IL-1ra reveal closely similar folds (Priestle et al. (1989) PNAS USA 86: 9667-967); Vigers et al. (1994) Biol Chem 269: 12874-12879). Structurally, the proteins consist of a single domain of 12 packed β-sheets known as a beta-trefoil. Since most of the packing interactions feature main chain atoms, it has been argued that few invariable amino acid are residues required to produce the IL-1 fold, hence extensive diversification of the coding sequences of the genes has been possible. A very similar fold is achieved in soybean trypsin inhibitor without any detectable sequence similarity. All three proteins bind the only functional signaling receptor for IL-1, the type I IL-1 receptor (IL-1R1) (see Sims et al. (1993) PNAS USA 90: 6155-6159).

IL-1 has been characterized mainly as the product of stimulated monocytes, macrophages and keratinocytes, but important roles have been suggested for IL-1 released from smooth muscle and endothelial cells (reviewed by Ross (1993) Nature 362: 801-9). Signaling through IL-1R1 involves the cytoplasmic Toll-like domain of the receptor (Heguy et al. (1992) J Biol Chem 267: 2605-2609). Functional IL-1 receptors are widely distributed in tissues. It is currently believed that IL-1ra differs from IL-1 in failing to activate the interaction between IL-1R1 and the second receptor component, IL-1 receptor accessory protein, IL-1RacP. This is a transmembrane protein that is a distant relative of IL-1R1, having a similar domain structure, but has no intrinsic affinity for IL-1 (Greenfeder et al. (1995) J Biol Chem 270: 13757-13756; Wesche et al., (1997) J Biol Chem 272: 7727-7731).

The IL-1 gene cluster is on the long arm of chromosome 2 (2q13) and contains at least the genes for IL-1α (IL-1A), IL-1β (IL-1B), and the IL-1 receptor antagonist (IL-1RN), within a region of 430 Kb (Nicklin, et al. (1994) Genomics, 19: 382-4). The maximum separation of the distal genes IL1A and IL1RN has been estimated to be 430 kb by pulse field gel electrophoresis of restriction digests of human genomic DNA (Nicklin, et al. (1994) Genomics, 19: 382-4), and the orientation of the three genes has been determined by sequence analysis of physical clones (Nothwang et al. (1997) Genomics 41: 370-378).

There are more than five million Type II (adult onset) diabetics diagnosed in the United States. Type II disease usually begins during middle age; the exact cause is unknown. In Type II diabetics, rising blood glucose levels after meals do not properly stimulate insulin production by the pancreas. Additionally, peripheral tissues are generally resistant to the effects of insulin. The resulting high blood glucose levels (hyperglycemia) can cause extensive tissue damage. Type II diabetics are often referred to as insulin resistant. They often have higher than normal plasma insulin levels (hyperinsulinomia) as the body attempts to overcome its insulin resistance. Some researchers now believe that hyperinsulinomia may be a causative factor in the development of high blood pressure, high levels of circulating low density lipo-proteins (LDLs), and lower than normal levels of the beneficial high density lipo-proteins (HDLs). While moderate insulin resistance can be compensated for in the early stages of Type II diabetes by increased insulin secretion, in advanced disease states insulin secretion is also impaired.

Insulin resistance and hyperinsulinomia have also been linked with two other metabolic disorders that pose considerable health risks: impaired glucose tolerance and metabolic obesity. Impaired glucose tolerance is characterized by normal glucose levels before eating, with a tendency toward elevated levels (hyperglycemia) following a meal. According to the World Health Organization, approximately 11% of the U.S. population between the ages of 20 and 74 are estimated to have impaired glucose tolerance. These individuals are considered to be at higher risk for diabetes and coronary artery disease.

Obesity may also be associated with insulin resistance. A causal linkage among obesity, impaired glucose tolerance, and Type II diabetes has been proposed, but a physiological basis has not yet been established. Some researchers believe that impaired glucose tolerance and diabetes are clinically observed and diagnosed only later in the disease process after a person has developed insulin resistance and hyperinsulinomia.

Insulin resistance is frequently associated with hypertension, coronary artery disease (arteriosclerosis), and lactic acidosis, as well as related disease states. The fundamental relationship between these disease states, and a method of treatment, has not been established.

Associated with insulin resistance is metabolic syndrome. Metabolic syndrome describes several cardiovascular risk factors that are associated with metabolic and inflammatory abnormalities including insulin resistance and obesity. It is believed that this syndrome may have a genetic component.

Recognizing that the entire IL-1 gene locus is centrally involved in inflammatory disease, we herein provide further detailed IL-1 locus polymorphism, linkage, disease association and functional analysis supporting compositions for detecting genetic identity at the human IL-1 locus and their use for the prediction, diagnosis and therapy of insulin resistance, type II diabetes, obesity, and metabolic disorder.

SUMMARY OF THE INVENTION

The invention provides a method for determining whether a subject is more likely to have or is predisposed to developing insulin resistance comprising detecting at least one allele selected from the group consisting of allele 1 of IL-1B (−511), allele 2 of IL-1A (+4845) and allele 2 of IL-1B (+3954) in the subject, wherein the subject who possesses one of the alleles is more likely to have or is predisposed to developing diabetes when compared to individuals who do not possess the alleles. In one embodiment of the method for determining whether a subject is more likely to have or is predisposed to developing insulin resistance, the insulin resistance is associated with type 2 diabetes or metabolic syndrome.

In another embodiment of the method for determining whether a subject is more likely to have or is predisposed to developing insulin resistance, the subject possesses two alleles selected from the group consisting of allele 1 of IL-1B (−511), allele 2 of IL-1A (+4845) and allele 2 of IL-1B (+3954), wherein a subject who possesses two of the alleles is more likely to have or is predisposed to developing diabetes when compared to individuals who are do not possess the alleles. In another embodiment of the method for determining whether a subject is more likely to have or is predisposed to developing insulin resistance, the subject possesses the alleles selected from the group consisting of allele 1 of IL-1B (−511), allele 2 of IL-1A (+4845) and allele 2 of IL-1B (+3954), wherein a subject who possesses the alleles is more likely to have or is predisposed to developing diabetes when compared to individuals who are do not possess the alleles.

The invention also provides a method for determining whether a subject is likely to have or is predisposed to developing insulin resistance through an increased expression level of IL-1β protein comprising detecting a LD Block 1 1/1 allele in the subject, wherein the increased expression level of IL-1β protein is increased in relation to subjects who do not possess the LD Block 1 1/1 allele. In one embodiment of the method for determining whether a subject is likely to have or is predisposed to developing insulin resistance through an increased expression level of IL-1β, the insulin resistance is associated with type 2 diabetes or metabolic syndrome.

In another embodiment of the method for determining whether a subject is likely to have or is predisposed to developing insulin resistance through an increased expression level of IL-1β, the LD Block 1 1/1 allele is performed by detecting a two copies of allele 1 of IL-1B (−511).

The invention also provides a method for determining whether a subject is likely to have or is predisposed to developing insulin resistance through an increased expression level of C-reactive protein comprising detecting a LD Block 2+allele in the subject, wherein the increased expression level of C-reactive protein is increased in relation to subjects who do not possess the LD Block 2+allele. In one embodiment of the method for determining whether a subject is likely to have or is predisposed to developing insulin resistance through an increased expression level of C-reactive protein, the insulin resistance is associated with type 2 diabetes or metabolic syndrome.

In another embodiment of the method for determining whether a subject is likely to have or is predisposed to developing insulin resistance through an increased expression level of C-reactive protein, the LD Block 2+allele is performed by detecting at least one allele 2 of IL-1A (+4845) and IL-1B (+3954) and two copies of allele 1 of IL-1B (+3877).

The invention also provides a method for determining whether a subject is likely to have or is predisposed to developing insulin resistance through an increased expression level of IL-1β protein comprising detecting a genotype selected from the group consisting of B1/B1, B1/B3 and B3/B3, wherein the increased expression level of IL-1β protein is increased in relation to subjects who do not possess any of the B1/B1, B1/B3 or B3/B3 genotypes. In one embodiment of the method for determining whether a subject is likely to have or is predisposed to developing insulin resistance through an increased expression level of IL-1β protein, the insulin resistance is associated with type 2 diabetes or metabolic syndrome.

In another embodiment of the method for determining whether a subject is likely to have or is predisposed to developing insulin resistance through an increased expression level of IL-1β protein, the detection of the genotype selected from the group consisting of B1/B1, B1/B3 and B3/B3 is performed by detecting two copies of allele 1 of IL-1B (−511). In another embodiment of the method for determining whether a subject is likely to have or is predisposed to developing insulin resistance through an increased expression level of IL-1β protein, the detection of the genotype selected from the group consisting of B1/B1, B1/B3 and B3/B3 is performed by detecting two copies of allele 1 of IL-1B (−1464).

The invention also provides a method for determining whether a subject is likely to have or is predisposed to developing insulin resistance through an increased expression level of C-reactive protein comprising detecting a genotype selected from the group consisting of B3/B3, B2/B3 and B4/B3 in the subject, wherein the increased expression level of C-reactive protein is increased in relation to subjects who do not possess any of the B3/B3, B2/B3 or B4/B3 genotypes. In one embodiment of the method for determining whether a subject is likely to have or is predisposed to developing insulin resistance through an increased expression level of C-reactive protein, the insulin resistance is associated with type 2 diabetes or metabolic syndrome.

In another embodiment of the method for determining whether a subject is likely to have or is predisposed to developing insulin resistance through an increased expression level of C-reactive protein, the detection of the genotype selected from the group consisting of B3/B3, B2/B3 and B4/B3 is performed by detecting two copies of allele 1 of IL-1B (−3737).

The invention also provides a method of treating insulin resistance in a subject in need thereof, by detecting predisposition to diabetes in the subject and administering to the subject, with a predisposition to insulin resistance, at least one anti-inflammatory therapy. In one embodiment of the method of treating insulin resistance in a subject in need thereof, the anti-inflammatory therapy is selected from the group consisting of an IL-1B neutralizing compound, an IL-6 neutralizing compound and a C-reactive protein neutralizing compound.

In another embodiment of the method of treating insulin resistance in a subject in need thereof, the neutralizing compounds are antibodies. In another embodiment of the method of treating insulin resistance in a subject in need thereof, the anti-inflammatory therapy is selected from the group consisting of diet, exercise, and nutraceuticals. In another embodiment of the method of treating insulin resistance in a subject in need thereof, the insulin resistance is associated with type 2 diabetes or metabolic syndrome. In another embodiment of the method of treating insulin resistance in a subject in need thereof, the predisposition to insulin resistance in the subject is detected by detecting the presence of a member selected from the group consisting of allele 1 of IL-1B (−511), allele 2 of IL-1A (+4845), allele 2 of IL-1B (+3954), two copies of allele 1 of IL-1B (−3737), and two copies of allele 1 of IL-1B (−1464).

The invention also provides a kit for the treatment of insulin resistance comprising a first nucleic acid of at least 12 contiguous nucleotides that hybridizes to a first target nucleic acid sequence position selected from the group consisting of a C at position −511 of the IL-1B gene and a C at position −3737 of the IL-1B gene, wherein said first nucleic acid hybridizes to said first target nucleic acid sequence at the position, or the complement of said first target nucleic acid sequence and at least one anti-inflammatory therapy, in one or more containers and instructions for use. In one embodiment of the kit, the kit further comprises a second nucleic acid at least 12 contiguous nucleotides that hybridizes to a second target nucleic acid sequence comprising a SNP selected from the group consisting of IL-1B (+3837), IL-1B (−511), IL-1B (+3954), IL-1RN (+2018), IL-1B (−1464) and IL-1A (+4845), or the complement of said second target nucleic acid sequence.

In another embodiment of the kit, the anti-inflammatory therapy is selected from the group consisting of an IL-1B neutralizing compound, an IL-6 neutralizing compound and a C-reactive protein neutralizing compound. In one aspect of this embodiment, the neutralizing compounds are antibodies. In another embodiment of the kit, the anti-inflammatory therapy is selected from the group consisting of diet, exercise, and nutraceuticals. In another embodiment of the kit, the insulin resistance is associated with type 2 diabetes or metabolic syndrome.

The invention also provides a kit for the detection of a predisposition to insulin resistance comprising a first nucleic acid of at least 12 contiguous nucleotides that hybridizes to a first target nucleic acid sequence position selected from the group consisting of a C at position −511 of the IL-1B gene and a C at position −3737 of the IL-1B gene, wherein said first nucleic acid hybridizes to said first target nucleic acid sequence at the position, or the complement of said first target nucleic acid sequence. In one embodiment of the kit, the kit further comprises a second nucleic acid at least 12 contiguous nucleotides that hybridizes to a second target nucleic acid sequence comprising a SNP selected from the group consisting of IL-1B (+3837), IL-1B (−511), IL-1B (+3954), IL-1RN (+2018), IL-1B (−1464) and IL-1A (+4845), or the complement of said second target nucleic acid sequence.

The invention also provides a method for determining whether a subject is likely to have or is predisposed to developing insulin resistance through an increased expression level of C-reactive protein comprising detecting a B212 haplotype in the subject, wherein the increased expression level of C-reactive protein is increased in relation to subjects who do not possess the B212 haplotype. In one embodiment, the subject is Asian or of Asian descent. In another embodiment, the subject is Korean or of Korean descent.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Figure 1:
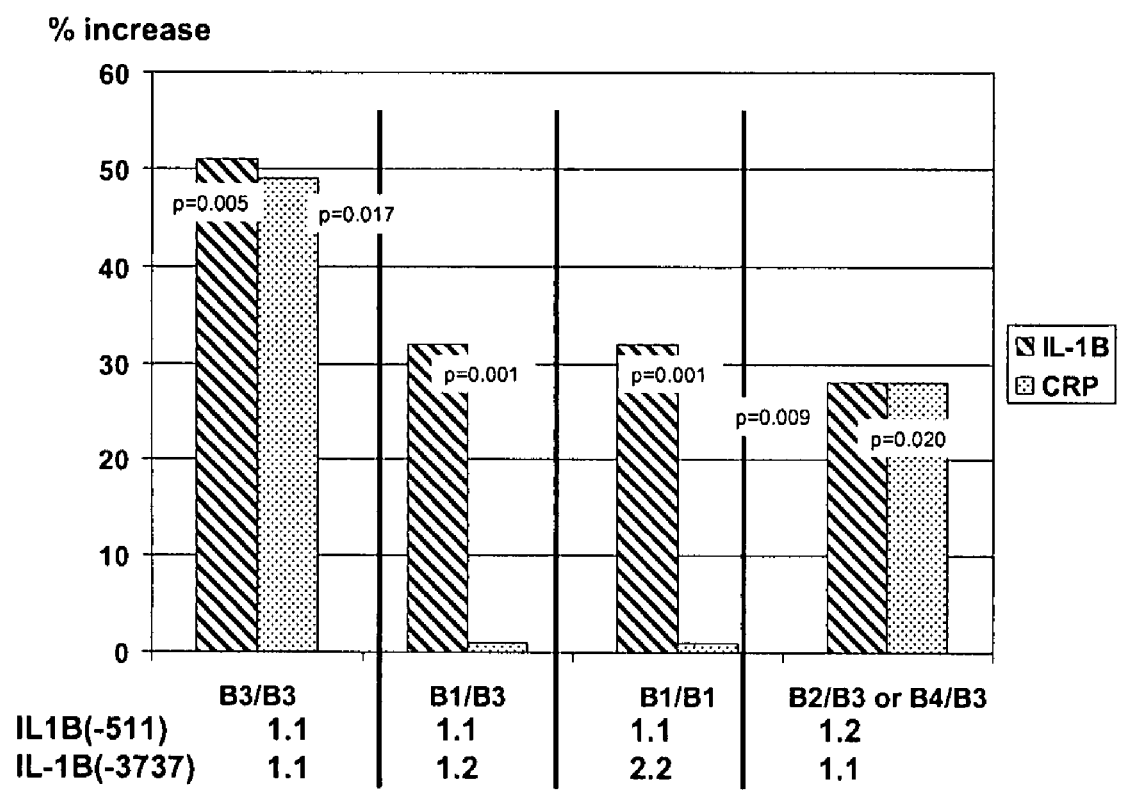
FIG. 1 is an exemplary plot illustrating percent increase of IL-1β and C-reactive protein for pro-inflammatory IL1B haplotype pairs relative to all others.

The methods and compositions of the invention provide correlations between the existence of certain IL-1 genotypes in a subject and the predisposition of subjects with these genotypes to have insulin resistance, type II diabetes, obesity, and/or metabolic disorder.

Interleukin-1β (IL-1β) is a potent cytokine involved in critical pathobiological processes of inflammation including activation of downstream mediators such as IL-6 and CRP. Extracellular release of IL-1β is regulated by complex feedback loops involving both the IL-1B gene, encoding the pro-inflammatory cytokine, as well as the IL-1RN gene encoding its natural antagonist.

There are primarily two regions within the IL-1 cluster of genes that control the level of inflammation in a subject. SNPs in the IL-1 cluster exhibit strong linkage disequilibrium (LD). Table 1 shows two blocks of SNPs in LD.

TABLE 1

| IL-1A | IL-1B | | IL-1 RN |
|---|---|---|---|
| +4845 | +3954 +3877 | −511 | +2018 |
| LD Block 2 | | LD Block 1 | |

LD Block 1 contains IL-1B (−511), which is associated with risk of myocardial infarction and IL-1β release from PBMC (Iacoviello, Arterioscler Thromb Vasc Biol. 2005 January; 25 (1):222-7). LD Block 2 contains SNPs associated with elevated C-reactive protein (CRP) and/or fibrinogen (Berger, Cytokine. 2002 Feb. 21; 17 (4):171-4; Latkovskis, Eur J Immunogenet. 2004 October; 31 (5):207-13). The LD Block 1 (LD #1) genotype is 1/1, 1/2 , or 2/2 , is generally associated with the genotype (1/1, 1/2 or 2/2 ) of IL-1B (−511). However, the LD #1 genotype is more nuanced, as described in greater detail below.

The LD Block 2 (LD #2) "+" genotype contains allele 2 at both IL-1A (+4845) and IL-1B (+3954) and the allele pattern of 1/1 at IL-1B (+3877). All other genotypes at these positions are considered "−".

LD #1 has been linked to two blood markers of inflammation, IL-1β and CRP. LD #2 is linked only to CRP. Specifically, two composite genotypes, both with 1/1 at LD Block 1, are associated with high levels of IL-1β. Also, two composite genotypes, both with "+" at LD Block 2, are associated with high levels of CRP. In certain embodiments, these genotypes also include the IL-RN (+2018) allele.

Table 2 summarizes previous results regarding of IL-1β and C-reactive protein (CRP) (U.S. Ser. No. 11/586,995, filed Oct. 25, 2006, U.S. Patent Application Publication No. 20070264645A1, now abandoned).

TABLE 2

| LD block 1 | LD block 2 | IL-1β | CRP |
|---|---|---|---|
| 1/1 | + | ↑ | ↑ |
| 1/1 | − | ↑ | |
| 1/2 | + | | ↑ |
| 1/2 | − | | |
| 2/2 | + | | |
| 2/2 | − | | |

LD #1 can also be analyzed in a more detailed manner. LD #1 consists basically of variation at 3 sites in the IL-1B gene, and the patterns representing these variations have been labeled B1, B2, B3, as shown below.

TABLE 3

Promoter haplotypes.

| Haplotype | IL1B (−511) (C to T) | IL1B (−1464) (G to C) | IL1B (−3737) (C to T) |
|---|---|---|---|
| B1 | 1 | 1 | 2 |
| B2 | 2 | 2 | 1 |
| B3 | 1 | 1 | 1 |
| B4 | 2 | 1 | 1 |
| B5 | 1 | 2 | 1 |
| B6 | 1 | 2 | 2 |
| B7 | 2 | 1 | 2 |
| B8 | 2 | 2 | 2 |

Given the four observed haplotypes, there are ten possible three-SNP genotype patterns (ignoring phase) arising from these haplotypes (Table 4).

TABLE 4

Possible composite genotypes from four observed haplotypes.

| Haplotype pairs | IL-1B (−511) | IL-1B (−1464) | IL-1B (−3737) |
|---|---|---|---|
| B1/B1 | 1.1 | 1.1 | 2.2 |
| B1/B2 | 1.2 | 1.2 | 1.2 |
| B1/B3 | 1.1 | 1.1 | 1.2 |
| B1/B4 | 1.2 | 1.1 | 1.2 |
| B2/B2 | 2.2 | 2.2 | 1.1 |
| B2/B3 | 1.2 | 1.2 | 1.1 |
| B2/B4 | 2.2 | 1.2 | 1.1 |
| B3/B3 | 1.1 | 1.1 | 1.1 |
| B3/B4 | 1.2 | 1.1 | 1.1 |
| B4/B4 | 2.2 | 1.1 | 1.1 |

It has been found that haplotype pairs partition into three groups. The first group comprises any combination of B1 and B3 haplotypes. The second group includes individuals with one copy of B3 and one copy of either B2 or B4. The third group includes all other combinations.

The first group i.e. individuals with any combination of B1 and B3, is associated with the highest expression of IL-1β. The second group has lower expression of IL-1β than the first group but higher expression than the third group. Linear regression revealed that, relative to the third group (42.6% frequency), the first group (42.7% frequency) has a 33% increased IL-1β ($p<0.0001$) and the second group (14.8% frequency) has a 28% increased IL-1β ($p<0.01$). (U.S. Ser. No. 11/586,995, filed Oct. 25, 2006, U.S. Patent Application Publication No. 20070264645A1, now abandoned).

As described above, specific IL-1 LD #1 and LD #2 patterns, either alone or in combination, are associated with increased blood levels of key markers of inflammation. There has been some evidence that high levels of IL-1β and CRP are associated with the onset of metabolic syndrome (Austin et al. Diabetes 53:1166-1169 (April 2004), Gonzalez et al. Eur. J. Clin. Nutr. 1-8 (2006), Tang et al. Diabetes Care 29 (3):631-636 March 2006)) and diabetes (Thomas et al. Diabetes 53:113-121 (January 2004).

The instant application demonstrates that the same genotypes, described above, that give subjects a predisposition to higher levels of inflammatory cytokines also are correlated with a predisposition to insulin resistance, type II diabetes, obesity, and/or metabolic disorder. Subjects that have the LD #1 1/1 or 1/2 allele pattern and/or the LD #2+allele pattern are predisposed to having insulin resistance, type II diabetes, obesity, and/or metabolic disorder. Also, subjects that have any combination of B1 and B3 alleles are predisposed to having insulin resistance, type II diabetes, obesity, and/or metabolic disorder. Subjects that have any combination of B2 and B3 or B3 and B4 alleles are also predisposed to having insulin resistance, type II diabetes, obesity, and/or metabolic disorder.

Subjects that have one or more copies of allele 2 of IL-1A (+4845), one or more copies of allele 2 of IL-1B (+3954), one or more copies of allele 1 of IL-1B (+3877) or one or more copies of allele 1 of IL-1B (−511) are predisposed to having insulin resistance, type II diabetes, obesity, and/or metabolic disorder. Also, subjects that have one or more copies of allele 2 of IL-1A (+4845) and one or more copies of allele 2 of IL-1B (+3954) are predisposed to having insulin resistance, type II diabetes, obesity, and/or metabolic disorder. Subjects that have one or more copies of allele 2 of IL-1A (+4845) and one or more copies of allele 1 of IL-1B (−511) are also predisposed to having insulin resistance, type II diabetes, obesity, and/or metabolic disorder. Subjects that have one or more copies of allele 2 of IL-1B (+3954) and or one or more copies of allele 1 of IL-1B (−511) are predisposed to having insulin resistance, type II diabetes, obesity, and/or metabolic disorder. Subjects that have one or more copies of allele 2 of IL-1A (+4845), one or more copies of allele 2 of IL-1B (+3954) and one or more copies of allele 1 of IL-1B (−511) are also predisposed to having insulin resistance, type II diabetes, obesity, and/or metabolic disorder. Subjects that have one or more copies of allele 2 of IL-1A (+4845), one or more copies of allele 2 of IL-1B (+3954) and two copies of allele 1 of IL-1B (−511) are also predisposed to having insulin resistance, type II diabetes, obesity, and/or metabolic disorder.

Subjects that have one or more copies of allele 2 of IL-1A (+4845), one or more copies of allele 2 of IL-1B (+3954), one or more copies of allele 1 of IL-1B (+3877) or one or more copies of allele 1 of IL-1B (−511) are more likely than those without one or more of these alleles to have insulin resistance, type II diabetes, obesity, and/or metabolic disorder. Also, subjects that have one or more copies of allele 2 of IL-1A (+4845) and one or more copies of allele 2 of IL-1B (+3954) are more likely than those without one or more of these alleles to have insulin resistance, type II diabetes, obesity, and/or metabolic disorder. Subjects that have one or more copies of allele 2 of IL-1A (+4845) and one or more copies of allele 1 of IL-1B (−511) are also more likely than those without one or more of these alleles to have insulin resistance, type II diabetes, obesity, and/or metabolic disorder. Subjects that have one or more copies of allele 2 of IL-1B (+3954) and or one or more copies of allele 1 of IL-1B (−511) are also more likely than those without one or more of these alleles to have insulin resistance, type II diabetes, obesity, and/or metabolic disorder. Subjects that have one or more copies of allele 2 of IL-1A (+4845), one or more copies of allele 2 of IL-1B (+3954) and one or more copies of allele 1 of IL-1B (−511) are also more likely than those without one or more of these alleles to have insulin resistance, type II diabetes, obesity, and/or metabolic disorder. Subjects that have one or more copies of allele 2 of IL-1A (+4845), one or more copies of allele 2 of IL-1B (+3954) and two copies of allele 1 of IL-1B (−511) are also more likely than those without one or more of these alleles to have insulin resistance, type II diabetes, obesity, and/or metabolic disorder.

Subjects that have one or more copies of allele 2 of IL-1A (+4845), one or more copies of allele 2 of IL-1B (+3954), one or more copies of allele 1 of IL-1B (+3877) or one or more copies of allele 1 of IL-1B (−511) are more likely than those without these alleles to have insulin resistance, type II diabetes, obesity, and/or metabolic disorder. Also, subjects that have one or more copies of allele 2 of IL-1A (+4845) and one or more copies of allele 2 of IL-1B (+3954) are more likely than those without these alleles to have insulin resistance, type II diabetes, obesity, and/or metabolic disorder. Subjects that have one or more copies of allele 2 of IL-1A (+4845) and one or more copies of allele 1 of IL-1B (−511) are also more likely than those without these alleles to have insulin resistance, type II diabetes, obesity, and/or metabolic disorder. Subjects that have one or more copies of allele 2 of IL-1B (+3954) and or one or more copies of allele 1 of IL-1B (−511) are also more likely than those without these alleles to have insulin resistance, type II diabetes, obesity, and/or metabolic disorder. Subjects that have one or more copies of allele 2 of IL-1A (+4845), one or more copies of allele 2 of IL-1B (+3954) and one or more copies of allele 1 of IL-1B (−511) are also more likely than those without these alleles to have insulin resistance, type II diabetes, obesity, and/or metabolic disorder. Subjects that have one or more copies of allele 2 of IL-1A (+4845), one or more copies of allele 2 of IL-1B (+3954) and two copies of allele 1 of IL-1B (−511) are also more likely than those without these alleles to have insulin resistance, type II diabetes, obesity, and/or metabolic disorder.

Subjects with the B212 haplotype, i.e. IL-1B (−511) is allele 2 or "T"; IL-1B (−1464) is allele 1 or "G" and IL-1B (−3737) is allele 2 or "T", have traits that show that they are protected from metabolic syndrome and thus from diabetes and increased severity and occurrence of coronary artery disease (CAD). The B212 haplotype has been associated with lower triglycerides and higher HDL, which is the opposite of metabolic syndrome, characterized by high triglycerides and low HDL. The B212 haplotype is also associated with lower levels of CRP, showing that subjects with this haplotype have lower inflammation and thus lower occurrence of diabetes and CAD.

The instant application also shows that subjects with a genetic predisposition for insulin resistance, type II diabetes, obesity, and metabolic disorder also have higher baseline levels of the inflammatory markers CRP, IL-6 and IL-1Ra. As explained above, these subjects should also have a higher baseline level of IL-1β. Thus, subjects with insulin resistance, type II diabetes, obesity, and/or metabolic disorder may take pharmaceutical compounds that block or diminish the effects of CRP, IL-6, IL-1Ra or IL-1β in order to treat insulin resistance, type II diabetes, obesity, or metabolic disorder. These treatments should be particularly effective in subjects that have one of the high inflammation genotypes, described above, that associates these subjects with a predisposition for insulin resistance, type II diabetes, obesity, and/or metabolic disorder. The pharmaceutical compounds include nutraceuticals, agonists and antagonists of CRP, IL-6, IL-1Ra or IL-1β, and antisense and RNAi molecules that reduce expression of CRP, IL-6, IL-1Ra or IL-1β.

The instant application also teaches kits that may have means for detecting the high inflammation genotypes in subjects. These kits contain restriction enzymes and primers useful for the genetic screening needed to detect these genotypes. Some kits also include means for taking samples from a patient. These samples include any biological sample from which genomic DNA from the subjects may be isolated including blood, urine, saliva, lymph, skin, and hair. Some kits also contain one or more pharmaceutical compositions for the treatment of insulin resistance, type II diabetes, obesity, and metabolic disorder. The pharmaceutical compounds include nutraceuticals, agonists and antagonists of CRP, IL-6, IL-1Ra or IL-1β, and antisense and RNAi molecules that reduce expression of CRP, IL-6, IL-1Ra or IL-1β.

Definitions

For convenience, the meaning of certain terms and phrases employed in the specification, examples, and appended claims is provided below.

The term "allele" refers to the different sequence variants found at different polymorphic regions. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1A (+4845) allele 1, which is an allelic pattern having at least one copy of IL-1A (+4845) allele 1 at the IL-1A (+4845) gene loci. Alternatively, an allelic pattern may consist of either a homozygous or heterozygous state at a single polymorphic site. For example, IL-1A (+4845) allele 1/1 is an allelic pattern in which there are two copies of the first allele of IL-1A (+4845) that corresponds to the homozygous IL-1A (+4845) allele 1 state. Alternatively, an allelic pattern may consist of the identity of alleles at more than one polymorphic site.

The term "antibody" as used herein is intended to refer to a binding agent including a whole antibody or a binding fragment thereof which is specifically reactive with an IL-1β, IL-6 or CRP polypeptide. Antibodies can be fragmented using conventional techniques and the fragments screened for utility in the same manner as described above for whole antibodies. For example, $F(ab)_2$ fragments can be generated by treating an antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for an IL-1β, IL-6 or CRP polypeptide conferred by at least one CDR region of the antibody.

"Biological activity" or "bioactivity" or "activity" or "biological function", which are used interchangeably, for the purposes herein means an effector or antigenic function that is directly or indirectly performed by an IL-1β, IL-6 or CRP polypeptide (whether in its native or denatured conformation), or by any subsequence thereof. Biological activities include binding to a target peptide, e.g., an IL-1 receptor or causing symptoms associated with insulin resistance, type II diabetes, obesity, and/or metabolic disorder. An IL-1β, IL-6 or CRP bioactivity can be modulated by directly affecting an IL-1β, IL-6 or CRP polypeptide. Alternatively, an IL-1β, IL-6 or CRP bioactivity can be modulated by modulating the level of an IL-1β, IL-6 or CRP polypeptide, such as by modulating expression of an IL-1β, IL-6 or CRP gene.

As used herein the term "bioactive fragment of an IL-1β, IL-6 or CRP polypeptide" refers to a fragment of a full-length IL-1 polypeptide, wherein the fragment specifically mimics or antagonizes the activity of a wild-type IL-1 polypeptide.

The bioactive fragment preferably is a fragment capable of interacting with an interleukin receptor.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but are still included within the scope of the term as used herein.

A "chimera," "mosaic," "chimeric mammal" and the like, refers to a transgenic mammal with a knock-out or knock-in construct in at least some of its genome-containing cells.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The term "haplotype" as used herein is intended to refer to a set of alleles that are inherited together as a group (are in linkage disequilibrium) at statistically significant levels ($p_{corr}$<0.05). As used herein, the phrase "an IL-1 haplotype" refers to a haplotype in the IL-1 loci. An IL-1 inflammatory or proinflammatory haplotype refers to a haplotype that is indicative of increased agonist and/or decreased antagonist activities.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al., Genomics 19:382-84, 1994). The terms "IL-1A", "IL-1B", and "IL-1RN" as used herein refer to the genes coding for IL-1, IL-1, and IL-1 receptor antagonist, respectively. The gene accession number for IL-1A, IL-1B, and IL-1RN are X03833, X04500, and X64532, respectively.

"L-1 functional mutation" refers to a mutation within the IL-1 gene cluster that results in an altered phenotype (i.e. effects the function of an IL-1 gene or protein). Examples include: IL-1A (+4845) allele 2, IL-1B (+3954) allele 2, and IL-1B (−511) allele 1.

"IL-1X (Z) allele Y" refers to a particular allelic form, designated Y, occurring at an IL-1 locus polymorphic site in gene X, wherein X is IL-1A, B, or RN and positioned at or near nucleotide Z, wherein nucleotide Z is numbered relative to the major transcriptional start site, which is nucleotide +1, of the particular IL-1 gene X. As further used herein, the term "IL-1X allele (Z)" refers to all alleles of an IL-1 polymorphic site in gene X positioned at or near nucleotide Z. For example, the term "IL-1A (+4845) allele" refers to alternative forms of the IL-1A gene at marker +4845. "IL-1A (+4845) allele 1" refers to a form of the IL-1RN gene which contains a cytosine (G) at position +4845 of the sense strand. "IL-1A (+4845) allele 2" refers to a form of the IL-1RN gene which contains a thymine (T) at position +4845 of the plus strand. When a subject has two identical IL-1A alleles, the subject is said to be homozygous, or to have the homozygous state. When a subject has two different IL-1A alleles, the subject is said to be heterozygous, or to have the heterozygous state. The term "IL-1A (+4845) allele 2/2 " refers to the homozygous IL-1A (+4845) allele 2 state. Conversely, the term "IL-1A (+4845) allele 1/1" refers to the homozygous IL-1A (+4845) allele 1 state. The term "IL-1A (+4845) allele 1/2 " refers to the heterozygous allele 1 and 2 state.

The term "IL-1 phenotype" is meant to refer to any phenotype resulting from an IL-1 gene locus genetic identity—i.e. including increased and decreased predispositions to an inflammatory disease or condition as well as a "normal" (e.g. average or "wild type") associated likelihood of an inflammatory disease or disorder.

"IL-1 related" as used herein is meant to include all genes related to the human IL-1 locus genes on human chromosome 2 (2q 12-14). These include IL-1 genes of the human IL-1 gene cluster located at chromosome 2 (2q 13-14) which include. the IL-1A gene which encodes interleukin-1α, the IL-1B gene which encodes interleukin-1β, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1α, interleukin-1β, and interleukin-1RN are related in so much as they all bind to IL-1 type I receptors, however only interleukin-1α and interleukin-1β are agonist ligands which activate IL-1 type I receptors, while interleukin-1RN is a naturally occurring antagonist ligand. Where the term "IL-1" is used in reference to a gene product or polypeptide, it is meant to refer to all gene products encoded by the interleukin-1 locus on human chromosome 2 (2q 12-14) and their corresponding homologs from other species or functional variants thereof. The term IL-1 thus includes secreted polypeptides which promote an inflammatory response, such as IL-1a and IL-1β, as well as a secreted polypeptide which antagonize inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from an IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

An "IL-1 polypeptide" and "IL-1 protein" are intended to encompass polypeptides comprising the amino acid sequence encoded by the IL-1 genomic DNA sequences shown in FIGS. 1, 2, and 3, or fragments thereof, and homologs thereof and include agonist and antagonist polypeptides.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

"Decreased risk" refers to a statistically lower frequency of occurrence of the disease or condition in an individual carrying a particular polymorphic allele in comparison to the frequency of occurrence of the disease or condition in a member of a population that does not carry the particular polymorphic allele or in the population as a whole.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene, so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: IL-1RN 5'/neo/IL-1RN 3', where IL-1RN5' and IL-1RN 3', refer to genomic or cDNA sequences which are, respectively, upstream and downstream relative to a portion of the IL-1RN gene and where neo refers to a neomycin resistance gene. In another knock-out construct, a second selectable marker is added in a flanking position so that the gene can be represented as: IL-1RN/neo/IL-1RN/TK, where TK is a thymidine kinase gene which can be added to either the IL-1RN5' or the IL-1RN3' sequence of the preceding construct and which further can be selected against (i.e. is a negative selectable marker) in appropriate media. This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage disequilibrium". The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are 100% in linkage disequilibrium with the two most frequent alleles of IL-1RN (VNTR), which are allele 1 and allele 2.

The term "marker" refers to a sequence in the genome that is known to vary among individuals. For example, the IL-1RN gene has a marker that consists of a variable number of tandem repeats (VNTR).

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

A "non-human animal" of the invention includes mammals such as rodents, non-human primates, sheep, dogs, cows, goats, etc. amphibians, such as members of the *Xenopus* genus, and transgenic avians (e.g. chickens, birds, etc.). The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any member of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

The term "nutraceutical", as used herein includes the FDA definitions of foods and dietary supplements that may be of value in treating a disease or disorder—particularly a disease or disorder associated with an inflammatory disease. Accordingly, "nutracteuticals" include nutritional ingredients that can be used to achieve health benefits. These ingredients may be in "foods"—i.e. "functional foods" or in dietary supplements. In October 1994, the Dietary Supplement Health and Education Act ("DSHEA") was signed into law. DSHEA acknowledges that millions of consumers believe that dietary supplements may provide health benefits. Congress's intent in passing it was to strike a balance between consumer access to dietary supplements and FDA's authority to act against supplements that present safety problems or bear false or misleading labeling. DSHEA creates a new regulatory framework for the safety and labeling of dietary supplements. The FDA is committed to enforcing DSHEA in a manner that effectuates DSHEA. Accordingly, "nutraceuticals," as used herein, includes dietary supplements known in the art (e.g. vitamins, minerals, herbs, phytoestrogens, flavonoids, phenolics, anthocyanins, carotenoids, polymers of the above and other supplements) which are ingested and are intended to supplement the diet and include a "dietary ingredient." Dietary ingredients may include vitamins, minerals, herbs or other botanicals, amino acids, and dietary substances such as enzymes. Dietary ingredients also can be metabolites, constituents, extracts, concentrates, or combinations of these ingredients. Nutraceutical supplements come in forms including tablets, capsules, liquids, and bars.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of a subject's incidence of developing a particular disease (e.g. a vascular disease). The alleles are thus over-represented in frequency in individuals with disease as compared to healthy individuals. Thus, these alleles can be used to predict disease even in pre-symptomatic or pre-diseased individuals.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule to hybridize to at least approximately 6 consecutive nucleotides of a sample nucleic acid.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgene" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of an IL-1 polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques. The term is intended to include all progeny generations. Thus, the founder animal and all F1, F2, F3, and so on, progeny thereof are included.

The term "treating" as used herein is intended to encompass curing as well as ameliorating at least one symptom of a condition or disease.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

Detection of Alleles

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic—occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™. is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

For mutations that produce premature termination of protein translation, the protein truncation test (PTT) offers an efficient diagnostic approach (Roest, et. al., (1993) Hum. Mol Genet. 2:1719-21; van der Luijt, et. al., (1994) Genomics 20:1-4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment, the DNA sample is obtained from a bodily fluid, e.g, blood, obtained by known techniques (e.g. venipuncture) or saliva. Alternatively, nucleic acid tests can be performed on dry samples (e.g. hair or skin). When using RNA or protein, the cells or tissues that may be utilized must express an IL-1 gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of an IL-1 proinflammatory haplotype and having about 5, 10, 20, 25, or 30 nucleotides around the mutation or polymorphic region. In a preferred embodiment of the invention, several probes capable of hybridizing specifically to other allelic variants involved in a restenosis are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874-1878), transcriptional amplification system (Kwoh, D. Y. et al., 1989, Proc. Natl. Acad. Sci. USA 86:1173-1177), and Q-Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of an IL-1 proinflammatory haplotype under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele of an IL-1 proinflammatory haplotype is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed by Maxim and Gilbert ((1977) Proc. Natl. Acad Sci USA 74:560) or Sanger (Sanger et al (1977) Proc. Nat. Acad. Sci. USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127-162; and Griffin et al. (1993) Appl Biochem Biotechnol 38:147-159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl. Acad Sci USA 85:4397; and Saleeba et al (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on an allele of an IL-1 locus haplotype is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify an IL-1 locus allele. For example, single strand conformation polymorphism (SSCP) may be used to detect differences in electrophoretic mobility between mutant and wild type nucleic acids (Orita et al. (1989) Proc Natl. Acad. Sci. USA 86:2766, see also Cotton (1993) Mutat Res 285:125-144; and Hayashi (1992) Genet Anal Tech Appl 9:73-79). Single-stranded DNA fragments of sample and control IL-1 locus alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the movement of alleles in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265: 12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) Nature 324:163); Saiki et al (1989) Proc. Natl. Acad. Sci. USA 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437-2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. ((1988) Science 241:1077-1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923-27). In this method, PCR is used to achieve the exponential amplification of target DNA, which is then detected using OLA.

Several techniques based on this OLA method have been developed and can be used to detect alleles of an IL-1 locus haplotype. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Another embodiment of the invention is directed to kits for detecting a predisposition for developing a restenosis. This kit may contain one or more oligonucleotides, including 5' and 3' oligonucleotides that hybridize 5' and 3' to at least one allele of an IL-1 locus haplotype. PCR amplification oligonucleotides should hybridize between 25 and 2500 base pairs apart, preferably between about 100 and about 500 bases apart, in order to produce a PCR product of convenient size for subsequent analysis.

The design of oligonucleotides for use in the amplification and detection of IL-1 polymorphic alleles by the method of the invention is facilitated by the availability of both updated sequence information from human chromosome 2q13—which contains the human IL-1 locus, and updated human polymorphism information available for this locus. For example, the DNA sequence for the IL-1A, IL-1B and IL-1RN (GenBank Accession No. X03833), 2 (GenBank Accession No. X04500) and 3 (GenBank Accession No. X64532) respectively. Suitable primers for the detection of a human polymorphism in these genes can be readily designed using this sequence information and standard techniques known in the art for the design and optimization of primers sequences. Optimal design of such primer sequences can be achieved, for example, by the use of commercially available primer selection programs such as Primer 2.1, Primer 3 or GeneFisher (See also, Nicklin M. H. J., Weith A. Duff G. W., "A Physical Map of the Region Encompassing the Human Interleukin-1α, interleukin-1β, and Interleukin-1 Receptor Antagonist Genes" Genomics 19: 382 (1995); Nothwang H. G., et al. "Molecular Cloning of the Interleukin-1 gene Cluster: Construction of an Integrated YAC/PAC Contig and a partial transcriptional Map in the Region of Chromosome 2q13" Genomics 41:370 (1997); Clark, et al. (1986) Nucl. Acids. Res., 14:7897-7914 [published erratum appears in Nucleic Acids Res., 15:868 (1987) and the Genome Database (GDB) project at the URL www.gdb.org).

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, the AmpliCard™ (University of Sheffield, Sheffield, England S10 2JF; Tarlow, J W, et al., J of Invest. Dermatol. 103:387-389 (1994)) and the like; DNA purification reagents such as Nucleon™ kits, lysis buffers, proteinase solutions and the like; PCR reagents, such as 10× reaction buffers, thermostable polymerase, dNTPs, and the like; and allele detection means such as the HinfI restriction enzyme, allele specific oligonucleotides, degenerate oligonucleotide primers for nested PCR from dried blood.

Pharmacogenomics

Knowledge of the particular alleles associated with a susceptibility to developing a particular disease or condition, alone or in conjunction with information on other genetic defects contributing to the particular disease or condition allows a customization of the prevention or treatment in accordance with the individual's genetic profile, the goal of "pharmacogenomics". Thus, comparison of an individual's IL-1 profile to the population profile for insulin resistance, type II diabetes, obesity, or metabolic disorder, permits the selection or design of drugs or other therapeutic regimens that are expected to be safe and efficacious for a particular patient or patient population (i.e., a group of patients having the same genetic alteration).

In addition, the ability to target populations expected to show the highest clinical benefit, based on genetic profile can enable: 1) the repositioning of already marketed drugs; 2) the rescue of drug candidates whose clinical development has been discontinued as a result of safety or efficacy limitations, which are patient subgroup-specific; and 3) an accelerated and less costly development for candidate therapeutics and more optimal drug labeling (e.g. since measuring the effect of various doses of an agent on the causative mutation is useful for optimizing effective dose).

The treatment of an individual with a particular therapeutic can be monitored by determining protein (e.g. IL-1α, IL-1β, or IL-1Ra), mRNA and/or transcriptional level. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level or amount of a protein, mRNA or genomic DNA in the preadministration sample; (iii) obtaining one or more post-administration samples from the subject; (iv) detecting the level of expression or activity of the protein, mRNA or genomic DNA in the post-administration sample; (v) comparing the level of expression or activity of the protein, mRNA or genomic DNA in the preadministration sample with the corresponding protein, mRNA or genomic DNA in the postadministration sample, respectively; and (vi) altering the administration of the agent to the subject accordingly.

Cells of a subject may also be obtained before and after administration of a therapeutic to detect the level of expression of genes other than an IL-1 gene to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

Therapeutics For Insulin Resistance, Type II Diabetes, Obesity, and Metabolic Disorder Therapeutics for insulin resistance, type II diabetes, obesity, and/or metabolic disorder refers to any agent or therapeutic regimen (including pharmaceuticals, nutraceuticals and surgical means) that prevents or postpones the development of or alleviates the symptoms of insulin resistance, type II diabetes, obesity, and/or metabolic disorder. The therapeutic can be a polypeptide, peptidomimetic, nucleic acid or other inorganic or organic molecule, preferably a "small molecule" including vitamins, minerals and other nutrients. Preferably the therapeutic can modulate at least one activity of an IL-1 polypeptide, for example IL-1β, CRP or IL-6 by, e.g., interaction with a receptor, mimicking or potentiating (agonizing) or inhibiting (antagonizing) the effects of a naturally-occurring polypeptide. An agonist can be a wild-type protein or derivative thereof having at least one bioactivity of the wild-type, e.g., receptor binding activity. An agonist can also be a compound that upregulates expression of a gene or which increases at least one bioactivity of a protein. An agonist can also be a compound which increases the interaction of a polypeptide with another molecule, e.g., a receptor. An antagonist can be a compound which inhibits or decreases the interaction between a protein and another molecule, e.g., a receptor or an agent that blocks signal transduction or post-translation processing (e.g., IL-1 converting enzyme (ICE) inhibitor). Accordingly, a preferred antagonist is a compound which inhibits or decreases binding to a receptor and thereby blocks subsequent activation of the receptor. An antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind to the active site of a protein and prevent it from interacting with target peptides. Yet other antagonists include antibodies that specifically interact with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site.

Modulators of IL-1 (e.g. IL-1α, IL-1β or IL-1 receptor antagonist), CRP or IL-6 or a protein encoded by a gene that is in linkage disequilibrium with an IL-1 gene can comprise any type of compound, including a protein, peptide, peptidomimetic, small molecule, or nucleic acid. Preferred agonists include nucleic acids (e.g. encoding an IL-1, CRP or IL-6 protein or a gene that is up- or down-regulated by an IL-1, CRP or IL-6 protein), proteins (e.g. IL-1, CRP or IL-6 proteins or a protein that is up- or down-regulated thereby) or a small molecule (e.g. that regulates expression or binding of an IL-1, CRP or IL-6 protein). Preferred antagonists, which can be identified, for example, using the assays described herein, include nucleic acids (e.g. single (antisense) or double stranded (triplex) DNA or PNA and ribozymes), protein (e.g. antibodies) and small molecules that act to suppress or inhibit IL-1, CRP or IL-6 transcription and/or protein activity.

Therapeutics for insulin resistance, type II diabetes, obesity, and/or metabolic disorder are effective in ameliorating any symptom associated with insulin resistance, type II diabetes, obesity, and/or metabolic disorder. These symptoms include frequent urination, excessive thirst, extreme hunger, unusual weight loss, increased fatigue, irritability, blurry vision, obesity, overweight, high blood sugar, cardiovascular disease, blindness, retinopathy, neuropathy, hyperinsulinomia, lactic acidosis, hypertension, impaired glucose tolerance, and kidney damage.

Effective Dose and Formulations and Use

Toxicity and therapeutic efficacy of such compounds can be determined by standard pharmaceutical procedures in cell cultures or experimental animals, e.g., for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ational oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Assays to Identify Therapeutics

Based on the identification of mutations that cause or contribute to the development of a disease or disorder that is associated with an IL-1 polymorphism or haplotype, the invention further features cell-based or cell free assays for identifying therapeutics. In one embodiment, a cell expressing an IL-1 receptor, or a receptor for a protein that is encoded by a gene which is in linkage disequilibrium with an IL-1 gene, on the outer surface of its cellular membrane is incubated in the presence of a test compound alone or in the presence of a test compound and another protein and the interaction between the test compound and the receptor or between the protein (preferably a tagged protein) and the receptor is detected, e.g., by using a microphysiometer (McConnell et al. (1992) Science 257:1906). An interaction between the receptor and either the test compound or the protein is detected by the microphysiometer as a change in the acidification of the medium. This assay system thus provides a means of identifying molecular antagonists which, for example, function by interfering with protein-receptor interactions, as well as molecular agonist which, for example, function by activating a receptor.

Cellular or cell-free assays can also be used to identify compounds which modulate expression of IL-1 (e.g. IL-1β), CRP or IL-6 genes or a gene in linkage disequilibrium therewith, modulate translation of an mRNA, or which modulate the stability of an mRNA or protein. Accordingly, in one embodiment, a cell which is capable of producing an IL-1 (e.g. IL-1β), CRP or IL-6, or other protein is incubated with a test compound and the amount of protein produced in the cell medium is measured and compared to that produced from a cell which has not been contacted with the test compound. The specificity of the compound vis a vis the protein can be confirmed by various control analysis, e.g., measuring the expression of one or more control genes. In particular, this assay can be used to determine the efficacy of antisense, ribozyme and triplex compounds.

Cell-free assays can also be used to identify compounds which are capable of interacting with a protein, to thereby modify the activity of the protein. Such a compound can, e.g., modify the structure of a protein thereby effecting its ability to bind to a receptor. In a preferred embodiment, cell-free assays for identifying such compounds consist essentially in a reaction mixture containing a protein and a test compound or a library of test compounds in the presence or absence of a binding partner. A test compound can be, e.g., a derivative of a binding partner, e.g., a biologically inactive target peptide, or a small molecule.

Accordingly, one exemplary screening assay of the present invention includes the steps of contacting a protein or functional fragment thereof with a test compound or library of test compounds and detecting the formation of complexes. For detection purposes, the molecule can be labeled with a specific marker and the test compound or library of test compounds labeled with a different marker. Interaction of a test compound with a protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the protein or functional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an IL-1 (e.g. IL-1β, CRP or IL-6 or other protein, (ii) an appropriate receptor, and (iii) a test compound; and (b) detecting interaction of the protein and receptor. A statistically significant change (potentiation or inhibition) in the interaction of the protein and receptor in the presence of the test compound, relative to the interaction in the absence of the test compound, indicates a potential antagonist (inhibitor). The compounds of this assay can be contacted simultaneously. Alternatively, a protein can first be contacted with a test compound for an appropriate amount of time, following which the receptor is added to the reaction mixture. The efficacy of the compound can be assessed by generating dose response curves from data obtained using various concentrations of the test compound. Moreover, a control assay can also be performed to provide a baseline for comparison.

Complex formation between a protein and receptor may be detected by a variety of techniques. Modulation of the formation of complexes can be quantitated using, for example, detectably labeled proteins such as radiolabeled, fluorescently labeled, or enzymatically labeled proteins or receptors, by immunoassay, or by chromatographic detection.

Typically, it will be desirable to immobilize either the protein or the receptor to facilitate separation of complexes from uncomplexed forms of one or both of the proteins, as well as to accommodate automation of the assay. Binding of protein and receptor can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase fusion proteins can be adsorbed onto glutathione sepharose beads (Sigma Chemical, St.

Louis, Mo.) or glutathione derivatized microtitre plates, which are then combined with the receptor, e.g. an $^{35}$S-labeled receptor, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of protein or receptor found in the bead fraction quantitated from the gel using standard electrophoretic techniques such as described in the appended examples. Other techniques for immobilizing proteins on matrices are also available for use in the subject assay. For instance, either protein or receptor can be immobilized utilizing conjugation of biotin and streptavidin. Transgenic animals can also be made to identify agonists and antagonists or to confirm the safety and efficacy of a candidate therapeutic. Transgenic animals of the invention can include non-human animals containing a restenosis causative mutation under the control of an appropriate endogenous promoter or under the control of a heterologous promoter.

The transgenic animals can also be animals containing a transgene, such as reporter gene, under the control of an appropriate promoter or fragment thereof. These animals are useful, e.g., for identifying drugs that modulate production of IL-1 (e.g. IL-1β, CRP or IL-6 proteins, such as by modulating gene expression. Methods for obtaining transgenic non-human animals are well known in the art. In preferred embodiments, the expression of the restenosis causative mutation is restricted to specific subsets of cells, tissues or developmental stages utilizing, for example, cis-acting sequences that control expression in the desired pattern. In the present invention, such mosaic expression of a protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of a mutation can be regulated via site-specific genetic manipulation in vivo, are known to those skilled in the art.

The transgenic animals of the present invention all include within a plurality of their cells a causative mutation transgene of the present invention, which transgene alters the phenotype of the "host cell". In an illustrative embodiment, either the cre/loxP recombinase system of bacteriophage P1 (Lakso et al. (1992) PNAS 89:6232-6236; Orban et al. (1992) PNAS 89:6861-6865) or the FLP recombinase system of *Saccharomyces cerevisiae* (O'Gorman et al. (1991) Science 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J Biol. Chem. 259:1509-1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the causative mutation transgene can be regulated via control of recombinase expression.

Use of the cre/loxP recombinase system to regulate expression of a causative mutation transgene requires the construction of a transgenic animal containing transgenes encoding both the Cre recombinase and the subject protein. Animals containing both the Cre recombinase and the restenosis causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonic target cells at various developmental stages can be used to introduce transgenes. Different methods are used depending on the stage of development of the embryonic target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BUJ6 or FVB lines are often used (Jackson Laboratory, Bar Harbor, Me.). Preferred strains are those with H-2$^b$, H-2$^d$ or H haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for microinjection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) PNAS 82:4438-4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83:9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984); U.S. Pat. No. 4,683,195; U.S. Pat. No. 4,683,202; and Nucleic Acid Hybridization (B. D. Hames & S. J. Higgins eds., 1984).

EXAMPLES

The following examples further support, but do not exclusively represent, preferred embodiments of the present invention.

Example 1

Genotyping Methods

Preparation of DNA

Blood is taken by venipuncture and stored uncoagulated at −20° C. prior to DNA extraction. Ten milliliters of blood are added to 40 ml of hypotonic red blood cell (RBC) lysis solution (10 mM Tris, 0.32 Sucrose, 4 mM $MgCl_2$, 1% Triton X-100) and mixed by inversion for 4 minutes at room temperature (RT). Samples are then centrifuged at 1300 g for 15 minutes, the supernatant aspirated and discarded, and another 30 ml of RBC lysis solution added to the cell pellet. Following centrifugation, the pellet is resuspended in 2 ml white blood cell (WBC) lysis solution (0.4 M Tris, 60 mM EDTA, 0.15 M NaCl, 10% SDS) and transferred into a fresh 15 ml polypropylene tube. Sodium perchlorate is added at a final concentration of 1 M and the tubes are first inverted on a rotary mixer for 15 minutes at RT, then incubated at 65° C. for 25 minutes, being inverted periodically. After addition of 2 ml of chloroform (stored at −20° C.), samples are mixed for 10 minutes at room temperature and then centrifuged at 800 g for 3 minutes. At this stage, a very clear distinction of phases can be obtained using 300 l Nucleon Silica suspension (Scotlab, UK) and centrifugation at 1400 g for 5 minutes. The resulting aqueous upper layer is transferred to a fresh 15 ml polypropylene tube and cold ethanol (stored at −20° C.) is added to precipitate the DNA. This is spooled out on a glass hook and transferred to a 1.5 ml eppendorf tube containing 500 μl TE or sterile water. Following overnight resuspension in TE, genomic DNA yield is calculated by spectrophotometry at 260 nm. Aliquots of samples are diluted at 100 μg/ml, transferred to microtiter containers and stored at 4° C. Stocks are stored at −20° C. for future reference.

Polymerase Chain Reaction

Oligonucleotide primers designed to amplify the relevant region of the gene spanning the polymorphic site (as detailed below) are synthesized, resuspended in Tris-EDTA buffer (TE), and stored at −20° C. as stock solutions of 200 μM. Aliquots of working solutions (1:1 mixture of forward and reverse, 20 μM of each in water) are prepared in advance.

Typically, PCR reaction mixtures are prepared as detailed below.

|  | Stock Concentration | Volume | Final Concentration |
|---|---|---|---|
| Sterile $H_2O$ |  | 29.5 μl |  |
| 10x PCR buffer | 200 mM Tris-HCl (pH 8.4) | 5.00 μl | 20 mM Tris-HCl, |
| $MgCl_2$ | 50 mM | 1.75 μl | 1.75 mM |
| dNTP | mix 10 mM of each | 4.00 μl | 0.2 mM of each |
| primer forward | 20 μM | 2.5 μl | 1 uM |
| prime reverse | 20 μM | 2.5 μl | 1 uM |
| Taq polymerase | 5 U/μl | 0.25 μl | 1.25 units/50 μl |
| Detergent (eg W-1, Gibco) | 1% | 2.5 μl | 0.05% |
| Template | 200 ng/μl | 2.00 μl | 2 ng/l |
| Final Volume |  | 50.00 μl |  |

DNA template is dotted at the bottom of 0.2 ml tubes or microwells. The same volume of water or negative control DNA is also randomly tested. A master-mix (including all reagents except templates) is prepared and added to the wells or tubes, and samples are transferred to the thermocycler for PCR.

PCR can be performed in 0.5 ml tubes, 0.2 ml tubes or microwells, according to the thermocycler available. The reaction mixture is overlaid with mineral oil if a heated lid (to prevent evaporation) is not available.

Restriction Enzyme Digestion

A master mix of restriction enzyme buffer and enzyme is prepared and aliquoted in suitable volumes in fresh microwells. Digestion is carried out with an oil overlay or capped microtubes at the appropriate temperature for the enzyme on a dry block.

Restriction buffer dilutions are calculated on the whole reaction volume (i.e. ignoring salt concentrations of PCR buffer). Restriction enzymes are used 3-5 times in excess of the recommended concentration to compensate for the unfavorable buffer conditions and to ensure complete digestion.

Electrophoresis

Polyacrylamide-gel electrophoresis (PAGE) of the PCR sample is carried out in Tris-Borate-EDTA buffer and at constant voltage. Depending on the size discrimination need, different PAGE conditions are used (9 to 12% acrylamide, 1.5 mm×200) and different DNA size marker (X174-Hae III or X 174-Hinf 1). A 2% agarose horizontal gel can be used for genotyping the IL-1RN (VNTR) marker.

Examples of IL-1 SNPs shown in Table 5.

TABLE 5

| Gene | Position | Nucleotide |
| --- | --- | --- |
| IL-1B | −511 | 1 = C, 2 = T |
| IL-1RN | +2018 | 1 = T, 2 = C |
| IL-1B | +3954 | 1 = C, 2 = T |
| IL-1B | +3877 | 1 = G, 2 = A |
| IL-1A | +4845 | 1 = G, 2 = T |
| IL-1B | −1464 | 1 = G, 2 = C |
| IL-1B | −3737 | 1 = C, 2 = T |

Generally, alleles are detected by PCR followed by a restriction digest or hybridization with a probe. Exemplary primer sets and analyses are presented for exemplary loci.

IL-1A (+4845). The IL-1A (+4845) marker may be genotyped in accordance with the following procedure. The PCR primers create an Fnu 4H1 restriction site in allele 1 to allow for RFLP analysis. The gene accession number is X03833. The oligonucleotide primers used for PCR amplification are:

(SEQ ID NO: 1)
5' ATG GTT TTA GAA ATC ATC AAG CCT AGG GCA 3'

(SEQ ID NO: 2)
5' AAT GAA AGG AGG GGA GGA TGA CAG AAA TGT 3'

MgCl$_2$ is used at 1 mM final concentration, and PCR primers are used at 0.8 µM. DMSO is added at 5% and DNA template is at 150 ng/50 µl PCR. Cycling is performed at [95° C., 1 min]×1; [94° C., 1 min; 56° C., 1 min; 72° C., 2 min]×35; [72° C., 5 min]×1; 4° C. To each PCR reaction is added 2.5 Units of Fnu 4H1 in addition to 2 µl of the specific 10× restriction buffer. Incubation is at 37° C. overnight. Electrophoresis is conducted by 9% PAGE.

Fnu 4H1 digest will produce a constant band of 76 bp (present regardless of the allele), and two further bands of 29 and 124 bp for allele 1, and a single further band of 153 bp for allele 2. Frequencies for the two alleles are 0.71 and 0.29.

IL-1B (−511). The IL-1B (−511) marker may be genotyped in accordance with the following procedure. The gene accession number is X04500. The oligonucleotide primers used for PCR amplification are:

5' TGG CAT TGA TCT GGT TCA TC 3'   (SEQ ID NO: 3)

5' GTT TAG GAA TCT TCC CAC TT 3'   (SEQ ID NO: 4)

MgCl$_2$ is used at 2.5 mM final concentration, and PCR primers are used at 1 µM. Cycling is performed at [95° C., 1 min]×1; [95° C., 1 min; 53° C., 1 min; 72° C., 1 min]×35; [72° C., 5 min]×1; 4° C. Each PCR reaction is divided into two aliquots: to one aliquot is added 3 Units of Ava I, to the other aliquot is added 3.7 Units of Bsu 36I. To both aliquots is added 3 µl of the specific 10× restriction buffer. Incubation is at 37° C. overnight. Electrophoresis is conducted by 9% PAGE.

Each of the two restriction enzymes cuts one of the two alleles, which allows for RFLP analysis. Ava I will produce two fragments of 190 and 114 bp with allele 1, and it does not cut allele 2 (304 bp). Bsu 36I will produce two fragments of 190 and 11 base pairs with allele 2, and it does not cut allele 1 (304 bp). Frequencies for the two alleles are 0.61 and 0.39.

IL-1B (+3954). The IL-1B (+3954) marker may be genotyped in accordance with the following procedure. The gene accession number is X04500. The oligonucleotide primers used for PCR amplification are:

(SEQ ID NO: 5)
5' CTC AGG TGT CCT CGA AGA AAT CAA A 3'

(SEQ ID NO: 6)
5' GCT TTT TTG CTG TGA GTC CCG 3'

MgCl$_2$ is used at 2.5 mM final concentration, and DNA template at 150 ng/50 µl PCR. Cycling is performed at [95° C., 2 min]×1; [95° C., 1 min; 67.5° C., 1 min; 72° C., 1 min]×35; [72° C., 5 min]×1; 4° C. To each PCR reaction is added 10 Units of Taq I (Promega) in addition to 3 µl of the specific 10× restriction buffer. Incubation is at 65° C. overnight. Electrophoresis is conducted by 9% PAGE.

The restriction enzyme digest produces a constant band of 12 bp and either two further bands of 85 and 97 bp corresponding to allele 1, or a single band of 182 bp corresponding to allele 2. Frequencies for the two alleles are 0.82 and 0.18.

IL-1B (−3737): Methods for detection of this allele are described in detail in U.S. provisional application No. 60/331,681, filed Nov. 19, 2001.

IL-1RN (+2018). PCR primers are designed (mismatched to the genomic sequence) to engineer two enzyme cutting sites on the two alleles to allow for RFLP analysis. The gene accession number is X64532. Oligonucleotide primers are:

5' CTATCTGAGGAACAACCAACTAGTAGC 3'   (SEQ ID NO: 7)

5' TAGGACATTGCACCTAGGGTTTGT 3'   (SEQ ID NO: 8)

Cycling is performed at [96° C., 1 min]; [94° C., 1 min; 57° C., 1 min; 70° C., 2 min;]×35; [70° C., 5 min]×1; 4° C. Each PCR reaction is divided in two 25 ul aliquots: to one is added 5 Units of Alu 1, to the other 5 Units of Msp 1, in addition to 3 ul of the specific 10× restriction buffer. Incubation is at 37° C. overnight. Electrophoresis is by PAGE 9%.

The two enzymes cut respectively the two different alleles. Alu 1 will produce 126 and 28 bp fragments for allele 1, while it does not digest allele 2 (154 bp). Msp I will produce 125 and 29 bp with allele 2, while allele 1 is uncut (154 bp). Hence the two reactions (separated side by side in PAGE) will give inverted patterns of digestion for homozygotes, and identical patterns in heterozygotes. Allelic frequencies are 0.74 and 0.26.

IL-1B (−3737) and IL-1B (−1464)

Genotyping was accomplished by performing separate polymerase chain reactions (PCR) specifically targeting the surrounding sequence for each SNP being studied. All PCR products from an individual sample were then combined, treated with exonuclease I and shrimp alkaline phosphatase (USB), and then diluted with Type I water. A multiplexed single base extension (SBE) reaction was then performed using Genome Lab SNPStart Primer Extension kit (Beckman-Coulter), the PCR products, and a mixture of SBE primers (each specifically targeting one SNP).

The SBE reaction adds a nucleotide specific fluorescent-labeled base to the 3' end of the SNP-specific primer. Two lasers subsequently detect the labeled primer after capillary separation within the Beckman Coulter CEQ8800 instrument. The results are analyzed by the software and are displayed as colored peaks—each color representing a different base. Presence of one single-colored peak indicates homozygote while two peaks of different colors indicate a heterozygote.

Samples are compared to a commercially available size standard that is run as a frame of reference. A sample of known genotype and a no template control are also run with each batch of samples as a measure of quality control.

The following primers, shown in Table 6, were used to detect the IL-1B (−3737) and IL-1B (−1464) alleles.

TABLE 6

| Primer Name | Sequence | Type | SEQ ID NO: |
|---|---|---|---|
| 3737_F1 | ACATCAGGGAAAAGCCATTG | PCR | 9 |
| 3737_R1 | TGGGAATGGGCACTATGATT | PCR | 10 |
| 1468_F1 | AAATCAGAAGGCTGCTTGGA | PCR | 11 |
| 1468_R1 | ATGGGTGAATGGGAATTTGA | PCR | 12 |
| SBE_1468-F1 | GCACAGAGGCTCACTCCCTTG | Genotype interogation | 13 |
| SBE_3737_R3 | GATTGGGGACATGCAGAGTCCAAGG | Genotype interogation | 14 |

Example 2

Subjects with High Inflammation Genotypes and Higher Levels of C-reactive Protein (CRP), IL-6 and IL-1ra Had Higher Baseline Insulin Levels and Higher Insulin Resistance than Subjects with Low Inflammation Genotypes As shown previously (U.S. Ser. No. 11/586,995, filed Oct. 25, 2006, U.S. Patent Application Publication No. 20070264645A1, now abandoned) alleles IL-1A (+4845) 1.2 or 2.2; IL-1B (+3954) 1.2 or 2.2; and IL-1B (−511) 1.1 are associated with higher levels of inflammation, as opposed to alleles IL-1A (+4845) 1.1; IL-1B (+3954) 1.1; IL-1B (−511) 1.2 or 2.2; and IL-1RN (+2018) 1.2 or 2.2. Female subjects who were overweight or mildly obese but otherwise in good health were selected for this study. All of the subjects were premenopausal, age 20-49 years, and the group of subjects had a mean BMI of 29. The subjects were genotyped to see if they fit into either of the higher or lower inflammation genotypes described above. The group genetically predisposed to higher levels of inflammation is referred to herein as the H group and the group genetically predisposed to lower levels of inflammation is referred to herein as the L group.

Subjects who did not fit into either group were excluded from the study. The H group contained 11 subjects and the L group contained 17 subjects. Two subjects were excluded from the H group because it was later found that they should have been excluded based on their genotype.

The subjects were put on an overnight fast, and then fed a high fat/high glucose meal. At baseline and during the following eight hours later, blood draws were taken and insulin levels were measured. The subjects in the H group showed a significantly higher baseline insulin level in their blood than subjects in the L group (12.20 vs. 8.80 µU/ml, p=0.046). The subjects in the H group also showed significantly more insulin resistance than subjects in the L group by two calculations involving baseline insulin +/−glucose values Formula 1:1/ fasting insulin, p=0.01, and Formula 2: 22.5/[fasting insulin× (fasting glucose/18.01)], p=0.03). (Florez J C, et al. N Engl J Med 2006; 355:241-50.) The subjects in the H group did not significantly different insulin secretion from the subjects in the L group (formulas involving baseline and 30 min time points).

Moreover, subjects in the H group had a higher baseline CRP, IL-6 and IL-1Ra levels than subjects in the L group. Also, subjects in the H group had higher stimulation of IL-6 release at 6 hrs.

Example 3

The Use of IL-1B Genotypes to Predict IL-1β and C-Reactive Protein Levels

Inflammation appears to be a central mechanism in the initiation and progression of multiple chronic diseases of aging. Among overtly healthy persons, some individuals are consistently in the upper range for certain inflammatory mediators, such as IL-1β and C-reactive protein (CRP). Moreover, compared to those in the lower end of the spectrum, these individuals are at increased risk for many diseases. Factors such as smoking, body mass index, and hormone replacement therapy explain a portion of the variance of inflammatory mediators in overtly healthy individuals, but genetic differences also appear to be an important determinant of inter-individual variance in inflammatory mediator levels. Here we show haplotypes that are correlated with increased IL-1β expression and increased CRP expression, leading to the correlation of these haplotypes, and the alleles contained within these haplotypes with inflammation and the initiation and progression of many chronic diseases associated with aging.

Inflammation is a major component of multiple diseases, and interleukin-1, which is regulated by the IL-1 gene cluster, is a primary initiator of the inflammatory process. Below we show that certain haplotype pairs of IL-1B are predictive of a higher expression of IL-1β in gingival crevicular fluid as well as higher levels of CRP in serum.

The study sample was selected from the Atherosclerosis Risk in Communities study (ARIC), as described below. The study sample, used below, comprises the 900 Caucasians from ARIC with both dental examinations and IL-1 genotypes. IL-1β levels from these subjects were assessed from samples of gingival crevicular fluid (GCF). Since the gingival crevice epithelium is in constant contact with a microbial biofilm, the level of IL-1β within the gingival crevicular fluid represents a serum transudate that is enriched by the local evoked gingival tissue response that has reached a steady state. Gingival crevicular fluid was collected as described in detail previously (Champagne et al., Periodontology 2000, 2003; 31: 167-180). Briefly, four GCF strips were eluted and analyzed separately (from the mesio-lingual of each first molar) from each subject and pooled to provide a patient mean value in pg/mL. IL-1β concentrations were measured on the GCF strip, using Enzyme-Linked Immunoadsorbent Assays (ELISA, Caymen Chemical Ann Arbor, Mich.).

C-reactive protein (CRP) in serum was measured, in these subjects, with a high sensitivity assay. Fasting blood samples were taken from all subjects and serum was frozen for subsequent analysis as previously described (Papp et al. Thrombosis & Haemostasis 1989 61 (1): 15-19). Serum C-reactive protein (CRP) concentrations were measured by latex-enhanced nephelometry (High Sensitivity CRP assay) on a BNII nephelometer (Dade Behring, Deerfield, Ill.). The BN II high sensitivity CRP assay utilizes a monoclonal antibody attached to polystyrene particles and fixed-time kinetic nephelometric measurements. This fully automated system creates a seven point standard curve from 0.4975 µg/ml (1:40 dilution of Rh Standard SL) to 0.0078 µg/ml (1:2560 dilution). The BN II makes a 1:400 dilution to measure sample CRP concentrations between 3.5 and 210 mg/L and a 1:20 dilution below 3.5 mg/L. This is an FDA, CLIA-complaint assay. Individuals with values above or below the limits of detection were excluded from analysis.

Since the GCF volume and protein composition is influenced by the local tissue inflammation, two periodontal endpoints were included in the study as covariates. One endpoint was the assessment of the percent of pocket depths of 4 or more millimeters. The second variable is composite measure of periodontal disease composed of pocket depth, bleeding on probing and interproximal attachment level of 3 millimeters or more measured on a 6-point ordinal scale. This composite measure is a more detailed version of an index developed to assess the inflammatory status of the periodontal tissue-biofilm interface (Offenbacher et al., Oral Biosci Med. 2005; 213:215-220).

Blood samples were collected in ethylenediaminetetraacetic acid (EDTA)-containing tubes and DNA was extracted for genotyping in the Division of Genomic Medicine, University of Sheffield, Sheffield UK. Blood used for plasma factors was centrifuged and frozen at –70° until analyzed. All genetic and blood analyses were performed by individuals unaware of other data.

Single nucleotide polymorphisms (SNPs) were tested at three locations within the IL-1B promoter, IL-1B (−511) (C→T transition), IL-1B (−1464) (G→C transition), and IL-1B (−3737) (C→T transition). Two additional SNPs, IL-1A (+4845) (G→T transition) and IL-1B (+3954) (C→T transition), were also genotyped to facilitate comparisons with other studies. The first nucleotide designated for each polymorphism is the common allele in Caucasians (e.g. −511C) and is referred to as "1", while the second nucleotide (e.g. −511T) is the less common allele and is termed "2". Genotyping was performed by Taqman™ 5' nuclease assay, as previously described (diGiovine et al., 2000 Detection and population analysis of IL-1 and TNF gene polymorphisms. In: Cytokine Molecular Biology. Oxford University Press, Oxford, UK Practical Approach Series, Chapter 2, pp. 21-46).

HAPLO.SCORE (Schaid, Am J Hum Genet, 2002; 70:425-434) was used to identify haplotype frequencies with non-negligible frequencies (>0.5%). Next, each possible pair of haplotypes drawn from this set were formed and determined whether the resulting haplotype-pair groups could be recreated unambiguously from phase unknown genotypes of the individual SNPs.

The overall null hypothesis of equal mean IL-1β levels across all haplotype pair groups was tested using analysis of variance (ANOVA) with degrees of freedom equal to the total number of groups minus one. The log-transformed values were used because of skewness in the distribution of IL-1β.

To identify specific haplotype groups associated with high IL-1β levels, mean levels of IL-1β were compared between each pair of haplotype groups. Next, the nominal p-values were calculated for each comparison the pairs were ranked from most to least significant. Finally, patterns of haplotypes clustering among the most significant pairs were sought.

Linear regression was used to estimate the magnitude of difference in IL-1β for different haplotype-pair groups. To do so, the set of non-genetic covariates was identified that associate with IL-1β. Then, with these covariates in the model, indicator variables for the haplotype pair groups were added. A similar approach was taken for CRP analysis except 1-sided p-values were calculated to reflect an a priori expectation of the direction of the effect based on the IL-1β results.

Demographic characteristics of the 900 Caucasian study participants are presented in Table 7. The study group was made up of 900 Caucasian subjects. Plus-minus values are ±SD.

TABLE 7

| Subject characteristics. | |
|---|---|
| Variable | |
| Age - yr | 61.7 ± 5.3 |
| Female sex - no. (%) | 498 (55) |
| Current smoker - no. (%) | 199 (22) |
| Diabetes - no. (%) | 133 (15) |
| Body mass index - kg/m² | 27.9 ± 5.0 |
| IL-1β - pg/mL | |
| Median | 155 |
| Interquartile range | 95-235 |
| C-reactive protein - mg/L | |
| Median | 4.2 |
| Interquartile range | 1.9-8.9 |

It has previously been reported that the gene for IL-1β had no detectable non-synonymous exonic SNPs and had four SNPs in the promoter-enhancer region that showed functional activity that was dependent on haplotype context. In multiple ethnic groups studied, two of the functional SNPs, IL-1B (−31) and IL-1B (−511) were perfectly concordant; therefore we used the three SNPs shown in Table 8 to characterize the functionally important IL-1B genetic variation. The nucleotide transition at the indicated locus shown has the first nucleotide as the most common allele, i.e. allele 1, in Caucasian populations. "ND" means that the allele was not detected in the study population.

TABLE 8

Promoter haplotype frequencies

| Haplotype | IL-1B (−511) (C to T) | IL-1B (−1464) (G to C) | IL-1B (−3737) (C to T) | Frequency |
|---|---|---|---|---|
| B1 | 1 | 1 | 2 | 46% |
| B2 | 2 | 2 | 1 | 28% |
| B3 | 1 | 1 | 1 | 20% |
| B4 | 2 | 1 | 1 | 6% |
| B5 | 1 | 2 | 1 | ND |
| B6 | 1 | 2 | 2 | ND |
| B7 | 2 | 1 | 2 | ND |
| B8 | 2 | 2 | 2 | ND |

Analysis of the 900 subject Caucasian population using HAPLO.SCORE (Schaid 2002) indicated that of the eight potential three-SNP haplotypes only four haplotypes were detected, which we have denoted B1, B2, B3, and B4 (Table 8).

Given the four observed haplotypes, there are ten possible three-SNP genotype patterns (ignoring phase) arising from these haplotypes (Table 9).

TABLE 9

Possible composite genotypes from 4 observed haplotypes

| Haplotype pairs | IL-1B (−511) | IL-1B (−1464) | IL-1B (−3737) | Frequency |
|---|---|---|---|---|
| B1/B1 | 1.1 | 1.1 | 2.2 | 22% |
| B1/B2 | 1.2 | 1.2 | 1.2 | 25% |
| B1/B3 | 1.1 | 1.1 | 1.2 | 17% |
| B1/B4 | 1.2 | 1.1 | 1.2 | 8% |
| B2/B2 | 2.2 | 2.2 | 1.1 | 7% |
| B2/B3 | 1.2 | 1.2 | 1.1 | 12% |
| B2/B4 | 2.2 | 1.2 | 1.1 | 3% |
| B3/B3 | 1.1 | 1.1 | 1.1 | 4% |
| B3/B4 | 1.2 | 1.1 | 1.1 | 2% |
| B4/B4 | 2.2 | 1.1 | 1.1 | <1% |

Because each of the ten haplotype pairs is unique, haplotypes can be assigned unambiguously for any individual. All of the ten possible composite genotype patterns were observed in the study population, but less than 1% of individuals (n=3) were homozygous for the B4 haplotype (Table 9). In addition, we point out that IL-1B (−511) and IL-1B (−1464) largely convey the same information in this population of Caucasians, as they are concordant in all haplotypes except for the least common, B4.

Correlating genotypes with IL-1 expression levels, the null hypothesis that the mean IL-1β protein levels (log IL-1β) were equal across the ten haplotype pairs shown in Table 9 was first tested. The null hypothesis was rejected (ANOVA; 9 degrees of freedom; p=0.005), indicating that there were significantly different IL-1β levels based on haplotype pairs. Exclusion of the small B4/B4 group did not impact this conclusion (p=0.003).

Having established an overall difference in the mean log of IL-1β across haplotype pair groups, we turned our attention to the identification of a specific set of haplotype pairs associated with high levels of this cytokine. To do this, we compared each haplotype pair against every other pair, producing comparisons and characterized the two tertiles of comparisons with the most significant p-values (Table 10). The gingival fluid log IL-1β protein concentration for individuals with each of the 10 possible IL-1 haplotype-pairs was compared to every other haplotype-pair, and the most significant comparisons are listed in order of nominal p-values. The first column from the left shows the haplotype-pair with the higher IL-1β protein in this specific comparison. The second column from the left shows the haplotype-pair with the lower IL-1β protein in this specific comparison. The column marked "Percent Higher" shows the mean percent increase in IL-1β protein level in individuals with the higher IL-1 haplotype-pair compared to individuals with the lower IL-1 haplotype-pair. The column marked "Rank" shows the relative rank of the 30 most significant haplotype-pair comparisons. The pairs marked with an asterisk (*) are the haplotype-pairs in the most significant comparisons that are comprised of genotype 1/1 at IL-1B (−511). The pairs marked with a dagger (†) are the haplotype-pairs in the most significant comparisons that are comprised of genotype 1/2 at IL-1B (−511) and 1/1 at IL-1B (−3737).

TABLE 10

| Higher Haplotype Pair | Lower Haplotype Pair | Percent Higher | Nominal p-value | Rank |
|---|---|---|---|---|
| B1/B1* | B1/B2 | 39% | 0 | 1 |
| B1/B3* | B1/B2 | 32% | 0.002 | 2 |
| B3/B3* | B1/B2 | 53% | 0.006 | 3.5 |
| B1/B1* | B1/B4 | 37% | 0.006 | 3.5 |
| B1/B1* | B2/B2 | 34% | 0.008 | 5 |
| B1/B3* | B1/B4 | 30% | 0.025 | 6 |
| B3/B3* | B1/B4 | 51% | 0.027 | 7 |
| B3/B3* | B2/B2 | 48% | 0.032 | 8.5 |
| B1/B3* | B2/B2 | 27% | 0.032 | 8.5 |
| B1/B1* | B2/B3† | 19% | 0.042 | 10 |
| B3/B4† | B1/B2 | 47% | 0.066 | 11 |
| B3/B3* | B2/B3 | 32% | 0.072 | 12 |
| B3/B4† | B1/B4 | 46% | 0.081 | 13.5 |
| B2/B3† | B1/B2 | 17% | 0.081 | 13.5 |
| B3/B4† | B2/B2 | 42% | 0.099 | 15 |
| B1/B1* | B2/B4 | 24% | 0.113 | 16 |
| B3/B3* | B2/B4 | 37% | 0.129 | 17 |
| B1/B3* | B2/B3† | 13% | 0.132 | 18 |
| B3/B4† | B2/B4 | 32% | 0.151 | 19 |
| B1/B1* | B4/B4 | 48% | 0.169 | 20 |
| B3/B3* | B1/B3* | 16% | 0.173 | 21 |
| B2/B3† | B1/B4 | 15% | 0.182 | 22 |
| B3/B4† | B2/B3† | 26% | 0.19 | 23 |
| B1/B3* | B2/B4 | 18% | 0.191 | 24 |
| B3/B4† | B4/B4 | 57% | 0.196 | 25 |
| B1/B3* | B4/B4 | 40% | 0.214 | 26 |
| B2/B3† | B2/B2 | 12% | 0.217 | 27.5 |
| B3/B3* | B4/B4 | 63% | 0.217 | 27.5 |

From this evaluation, we found haplotype pairs to partition very nicely into three groups. The first group comprises any combination of B1 and B3 haplotypes (marked with asterisks (*) in Table 10). The second group includes individuals with one copy of B3 and one copy of either B2 or B4 (marked with daggers (†) in Table 10). The third group includes all other combinations.

Of the 28 most significant haplotype-pair comparisons, the first group i.e. individuals with any combination of B1 and B3, occurs as the "high IL-1β" haplotype-pair 21 of 28 times and is never the "low IL-1β" haplotype-pair relative to any other haplotype pair. The second group i.e. individuals with one copy of B3 and one copy of either B2 or B4, occurs the remaining 9 of 28 times as the "high IL-1β" haplotype-pair and is the "low IL-1β" haplotype-pair in the most significant comparisons only when compared to the haplotype pairs in the first group. Linear regression revealed that, relative to the third group (42.6% frequency), the first group (42.7% frequency) has a 33% increased IL-1β (p<0.0001) and the second group (14.8% frequency) has a 28% increased IL-1β (p<0.01).

Gingival fluid is a serum transudate that also reflects the local periodontal tissue inflammation. Since levels of gingival fluid IL-1β are strongly associated with the severity of local periodontal disease, the analysis included adjustment for two periodontal disease severity endpoints available in this database: 1) percentage of periodontal pocket depths exceeding 4 mm, and 2) a composite measure of periodontal disease. With the two periodontal endpoints included in the model, no other covariates except for IL-1 genotypes were significant predictors of IL-1β levels in GCF.

The first group of IL-1β over-expressing haplotype-pairs translates more simply into carriage of 1/1 at IL-1B (−511). Equivalently, the second group includes those who are both 1/2 at IL-1B (−511) and 1/1 at IL-1B (−3737). Because the group comprising individuals with 1/1 at IL-1B (−511) is relatively large (>40% of this study population), we repeated our analysis splitting the group into its three haplotype pair groups: B3/B3, B1/B3, and B1/B1. Each of these components, as well as the B2/B3+B4/B3 group was significantly higher in IL-1β levels than the remaining individuals (FIG. 24). Interestingly, only two of these four groups were associated with increased serum CRP, namely B3/B3 and B2/B3+B4/B3 (FIG. 1).

The two groups associated with higher CRP levels are distinguished from the other pro-inflammatory patterns by homozygosity for the common allele (1/1) at IL-1B (−3737). The combined B3/B3 and B2/B3+B4/B3 group had 33% higher CRP values versus all others (p=0.007) after adjustment for BMI, smoking, and gender.

Two additional SNPs in the IL-1 gene cluster, IL-1A (+4845) and IL-1B (−3954), have been associated with differential expression of inflammatory mediators (Berger 2002) and clinical phenotypes, and typically carriage of the minor alleles has been reported to be pro-inflammatory. The frequency of carrying a minor allele at both IL-1A (+4845) and IL-1B (−3954) is 35% in our study population, but this frequency increases to 84% in the B3/B3 and B2/B3+B4/B3 group compared to 23% in others. In this data set CRP was less strongly associated with IL-1A (+4845), IL-1B (+3954), or composites of these two SNPs than the combined B3/B3 and B2/B3+B4/B3 group.

Another pro-inflammatory haplotype pair is characterized by a 1/2 genotype at IL-1B (−511) together with a 1/1 genotype at IL-1B (−3737). It has been reported that individuals with 1/2 at IL-1B (−511) are also at increased risk of both clinical and biochemical endpoints, but less significantly than those carrying 1/1 at IL-1B (−511). As shown herein, this intermediate risk group of heterozygotes is actually comprised of two distinct groups, one with 1/1 at IL-1B (−3737) and the other with 1/2 at IL-1B (−3737). The former, we speculate, would be associated with clinical endpoints and biochemical measurements, perhaps as significantly as those carrying 1/1 at IL-1B (−511), and the latter would be more similar to those with 2/2 at IL-1B (−511). In this Caucasian population approximately 47% of the individuals carried IL-1B (−511) genotype 1/2, which was divided between 14% of the population which also carried IL-1B (−3737) genotype 1/1 and 33% which also carried IL-1B (−3737) genotype 1/2. In this population, no individuals carried IL-1B (−511) genotype 1/2 and IL-1B (−3737) genotype 2/2.

Previous work has found that haplotypes with allele 2 (C nucleotide) at IL-1B (−1464) consistently showed decreased promoter activity in both single SNP and haplotype constructs. In Caucasians, most haplotypes with IL-1B (−511) allele 2 also included IL-1B (−1464) allele 2 (haplotype B2=28% vs. B4=6%. This is consistent with the observation in this study that genotypes composed of two copies of haplotype B2 had the lowest IL-1β levels. In addition, genotypes that included one copy of B2 showed higher levels of IL-1β only if they were also genotype 1/1 (C/C) at IL-1B (−3737).

NF-κB components show increased binding to IL-1B (−3737) allele 1 compared to allele 2, and allele 1 at this locus increased activity of promoter constructs in certain haplotypes.

IL-1B (−3737) also appears to be a key determinant of whether or not an IL-1B promoter pattern associated with high IL-1β is also associated with increased serum CRP levels. Specifically, individuals who carry at least one 2 allele at IL-1B (−3737) do not seem to manifest high CRP values, even if they have high IL-1β values. This may be due to potential temporal differences in IL-1β expression, and subsequent differential downstream effects, with haplotypes that include different IL-1B (−3737) alleles.

Multiple studies have reported association of other IL-1 SNPs with clinical outcomes and biochemical measurements. Frequently, authors have concluded that carriage of minor alleles at IL-1A (+4845) and/or IL-1B (+3954) represents a pro-inflammatory genotype. For example, allele 2 at IL-1B (+3954) is strongly associated with increased CRP in individuals presenting for cardiac catheterization. However, not all studies demonstrate such significance. One possibility is that IL-1A (+4845) and IL-1B (+3954) act only as surrogates for the causative genetic variants, possibly defined by IL-1B haplotype pair groups. In fact, among our haplotype pairs groups associated with elevated log IL-1β expression, 84% carried a minor allele at both IL-1A (+4845) and IL-1B (−3954) compared to 23% in the remaining haplotype pair groups.

Further, in order to validate the pro-inflammatory potential of the specific IL-1 haplotype-pairs found to be associated with higher levels of IL-1β in gingival transudates, PBMCs were collected from a separate population of individuals (n=70). The IL-1β production by PBMCs was analyzed after stimulation with lipopolysaccharide (LPS). These results are summarized in Table 11.

TABLE 11

IL-1β protein production by peripheral blood mononuclear cells from subjects with different IL-1B Haplotype-Pairs

| IL-1B promoter haplotype-pairs | N[2] | Mean IL-1β (ng/ml) difference after LPS stimulation[3] | SD[4] | Increase over reference[5] | P-value |
|---|---|---|---|---|---|
| B1/B1 | 20 | 2.51 | 3.18 | 199% | 0.002 |
| B1/B3 | 10 | 1.56 | 4.07 | 86% | 0.33 |
| B3/B3 | 4 | 3.25 | 2.11 | 287% | 0.019 |
| B3/B2 or B4 | 7 | 2.36 | 2.26 | 181% | 0.012 |
| Reference group[1] | 29 | 0.84 | 2.92 | | |
| Total | 70 | | | | |

[1]The reference group includes all possible pairs of IL-1B haplotypes B1 through B4, other than the four haplotype-pairs specified above
[2]Number of subjects with the indicated haplotype-pair
[3]Geometric mean difference of IL-1β protein produced by peripheral blood mononuclear cells (PBMCs) stimulated with lipopolysaccharide (LPS) compared to unstimulated baseline production (stimulated minus unstimulated). All assays were performed in duplicate by personnel blinded to the genotype.
[4]Standard deviation
[5]Percentage increase in IL-1β protein production by PBMCs from the indicated IL-1B haplotype-pair compared to the production by PBMCs from the reference group. e.g. ((B1/B1-difference after LPS stimulation) − reference group difference after LPS stimulation)/(reference group difference after LPS stimulation) = % increase; ((2.51−0.84)/0.84) = 1.99 × 100

Specifically, it had been determined that the four haplotype-pairs associated with higher in vivo IL-1β levels, stimulated PBMCs from three of the four groups produced significantly more IL-1β protein than cells from those with haplotype-pairs in the reference group. PBMCs from the fourth group produced more IL-1β protein than the reference group, but the difference was not significant.

Materials and Methods.

For these experiments, the in vivo study sample was selected from the Atherosclerosis Risk in Communities study (ARIC), a prospective investigation of atherosclerosis and its clinical sequelae. The ARIC population-based cohort contained 15,792 subjects aged 45-65 years, selected by probability sampling from four communities: Forsyth County, N.C.; Jackson, Miss.; Northwestern suburbs of Minneapolis, Minn.; and Washington County, Md. A detailed description of the ARIC study design and methods is published elsewhere (The ARIC Investigators, 1989). As part of an ancillary study of periodontal disease, a subset of the original ARIC population underwent dental examinations and a further subset was selected for IL-1 genotyping. The study sample comprised the 900 Caucasians from ARIC with both dental examinations and IL-1 genotypes.

Further, IL-1β levels were assessed from samples of gingival crevicular fluid (GCF). Since the gingival crevice epithelium is in constant contact with a microbial biofilm, the level of IL-1β within the GCF fluid represents a serum transudate that is enriched by the local evoked gingival tissue response that has reached a steady state. Thus, GCF was collected as described in detail previously. Briefly, four GCF strips were eluted and analyzed separately (from the mesio-lingual of each first molar) from each subject and pooled to provide a patient mean value in pg/mL. IL-1β concentrations were measured on the GCF strip, using Enzyme-Linked Immunoadsorbent Assays (ELISA, Caymen Chemical Ann Arbor, Mich.).

Another marker of inflammatory response, C-reactive protein (CRP) was monitored in the serum of the subject by a high sensitivity assay. Fasting blood samples were taken from all subjects and serum was frozen for subsequent analysis as previously described (Papp A C et al., Thromb Haemost 1989; 61 (1):15-9). Further, serum C-reactive protein (CRP) concentrations were measured by latex-enhanced nephelometry (High Sensitivity CRP assay) on a BNII nephelometer (Dade Behring, Deerfield, Ill.). The BN II high sensitivity CRP assay utilizes a monoclonal antibody attached to polystyrene particles and fixed-time kinetic nephelometric measurements. This fully automated system creates a seven point standard curve from 0.4975 μg/ml (1:40 dilution of Rh Standard SL) to 0.0078 μg/ml (1:2560 dilution). The BN II makes a 1:400 dilution to measure sample CRP concentrations between 3.5 and 210 mg/L and a 1:20 dilution below 3.5 mg/L. This is an FDA, CLIA-complaint assay. Individuals with values above or below the limits of detection were excluded from analysis.

Since the GCF volume and protein composition may be influenced by the local tissue inflammation, two periodontal endpoints were included in the study as covariates. One endpoint was the assessment of the percent of pocket depths of four or more millimeters. The second variable was a composite measure of periodontal disease composed of pocket depth, bleeding on probing and interproximal attachment level of three millimeters or more measured on a six-point ordinal scale. This composite measure was a more detailed version of an index developed to assess the inflammatory status of the periodontal tissue-biofilm interface.

Further, blood samples were collected in ethylenediaminetetraacetic acid (EDTA)-containing tubes and DNA was extracted for genotyping in the Division of Genomic Medicine, University of Sheffield, Sheffield UK. Blood used for plasma factors was centrifuged and frozen at −70° until analyzed. All genetic and blood analyses were performed by individuals unaware of other data.

During the course of the experiments, single nucleotide polymorphisms (SNPs) were tested at three locations within the IL-1B promoter, IL-1B (−511) (C→T transition), IL-1B (−1464) (G→C transition), and IL-1B (−3737) (C→T transition). Two additional SNPs, IL-1A (+4845) (G→T transition) and IL-1B (+3954) (C→T transition), were also genotyped to facilitate comparisons with other studies. The first nucleotide designated for each polymorphism is the common allele in Caucasians (e.g. −511C) and is referred to as "1", while the second nucleotide (e.g. −511T) is the less common allele and is termed "2". Genotyping was performed by TAQMAN™ 5' nuclease assay, as previously described (di Giovine F S et al., Cytokine Molecular Biology. Oxford: Oxford University Press; 2000).

The null hypothesis of equal mean IL-1β levels was tested across all haplotype-pair groups using analysis of variance (ANOVA) with degrees of freedom equal to the total number of groups minus one. For these experiments, the log-transformed values because of skewness in the distribution of IL-1β. Further, to identify specific haplotype groups associated with high IL-1β levels, mean levels of IL-1β were compared between each pair of haplotype groups. Next, nominal p-values were calculated for each comparison and ranked the pairs from most to least significant. Finally, the patterns of haplotypes clustering among the most significant pairs were searched.

To analyze data, the linear regression was used to estimate the magnitude of difference in IL-1β for different haplotype-pair groups. To do so, it was required to identify the set of non-genetic covariates that associate with IL-1β. Then, with these covariates in the model, indicator variables for the haplotype-pair groups were added. A similar approach was taken for CRP analysis except one-sided p-values were calculated to reflect an a priori expectation of the direction of the effect based on the IL-1β results.

For statistical analysis, P-values were used in three distinct ways in this report. First, for the overall test of equal mean IL-1β levels, they were used in the traditional hypothesis testing sense. That is, the p-value reflected the proportion of times one would expect a statistic as large as or larger than the one observed if the null hypothesis were true. Second, p-values were used as a device for ranking all pair-wise comparisons of haplotype pair groups. This allowed for search for patterns of haplotypes that underlie any overall significant differences. Finally, once haplotype pair groups were identified (hopefully with a discernable pattern of constituent haplotypes), p-values were calculated for the aggregate risk group compared to all other groups. These p-values did not take into account the multiple comparison issue inherent in such a grouping procedure.

Finally, effect of IL-1B haplotype-pairs on IL-1β release by peripheral blood mononuclear cells (PBMCs) was determined in healthy volunteers, using methods similar to previous descriptions (Iacoviello L, Arterioscler Thromb Vasc Biol 2005; 25 (1):222-7) Further, PBMCs were obtained from 75 volunteers, of which 70 had complete data and freshly drawn whole blood was processed as described previously (Napoleone et al., Circ Res 2000; 86 (2):139-43). The final mononuclear cell preparation was incubated with lipopolysaccharide (LPS; 0.1 microg/mL) for 24 hours. Cells were sedimented and IL-1β was measured in the supernatants by high-sensitivity ELISA (Amersham Pharmacia Biotech). Each experiment was performed in duplicate by operators blinded to sample identity.

The experiments described in this Example unequivocally demonstrate that an analysis using pairs of functional haplotypes identified IL-1 genotypes that were significantly associated with increased inflammatory biomarkers in vivo. This is the first demonstration of a relationship between in vivo levels of an inflammatory mediator and haplotypes of its gene promoter on both chromosomes. These findings may apply to other inducible genes and could provide a logical framework for exploring disease risk related to genetic variability in the production of pathogenic mediators.

Example 4

The B212 Haplotype Appears to be Protective for Cardiovascular Disease

The results of the experiments described in this Example, demonstrate that subjects with B212 haplotype exhibit lower levels of C-reactive protein in comparison to subjects without B212. It had been suggested that B212 is a protective haplotype against cardiovascular disease.

As shown previously (U.S. Ser. No. 11/586,995, filed Oct. 25, 2006, U.S. Patent Application Publication No. 20070264645A1, now abandoned) alleles IL-1B, 1.2 or 2.2; and IL-1B, 1.1 are associated with higher levels of inflammation, as opposed to alleles IL-1A 1.1; IL-1B 1.1 and IL-1B 1.2 or 2.2. This study demonstrates that subjects with B212 haplotype exhibit lower levels of C-reactive protein in comparison to subjects without B212 and suggests that B212 is a protective haplotype against insulin resistance, metabolic disorders and cardiovascular disorders.

In this study, the predisposition to metabolic and cardiovascular disorders was tested in 281 control and 291 Korean subjects with coronary artery disease (CAD). BMI (body mass index), BPS (systolic blood pressure), BPD (diastolic blood pressure), TG (triglycerides), TCHOL (total cholesterol), HDL (high density lipoprotein) and LDL (low density lipoprotein) were compared between control subjects and CAD subjects with and without the protective B212 haplotype.

Circulating cholesterol is carried by plasma lipoproteins—particles of complex lipid and protein composition that transport lipids in the blood. Low density lipoproteins (LDL), and high density lipoproteins (HDL) are the major cholesterol carriers. LDL are believed to be responsible for the delivery of cholesterol from the liver (where it is synthesized or obtained from dietary sources) to extrahepatic tissues in the body. The term "reverse cholesterol transport" describes the transport of cholesterol from extrahepatic tissues to the liver where it is catabolized and eliminated. It is believed that plasma HDL particles play a major role in the reverse transport process, acting as scavengers of tissue cholesterol.

The evidence linking elevated serum cholesterol to coronary heart disease is overwhelming. For example, atherosclerosis is a slowly progressive disease characterized by the accumulation of cholesterol within the arterial wall. Compelling evidence supports the concept that lipids deposited in atherosclerotic lesions are derived primarily from plasma LDL; thus, LDLs have popularly become known as the "bad" cholesterol. In contrast, HDL serum levels correlate inversely with coronary heart disease—indeed, high serum levels of HDL are regarded as a negative risk factor. It is hypothesized that high levels of plasma HDL are not only protective against coronary artery disease, but may actually induce regression of atherosclerotic plaques (e.g., see Badimon et al., 1992, Circulation 86 (Suppl. III): 86-94). Thus, HDL have popularly become known as the "good" cholesterol. Decreased HDL and increased TG are also associated with metabolic syndrome.

For these experiments, HDL, LDL and TG levels are isolated from serum using methods well known in the art. Genotyping was performed as described in Example 1.

As summarized in Tables 12 and 13, control subjects with B212 haplotype have a higher association with parameters predictive of lower risk of metabolic disorder and cardiovascular disease, such as lower total triglyceride levels, lower LDL levels and higher HDL levels as compared to control subjects without the protective B212 haplotype. Similar results were found for CAD subjects with protective B212 haplotype as compared to CAD subjects without protective B212 haplotype. Thus, CAD subjects with protective B212 haplotype exhibit lower TG values and higher HDL values compared to subjects without protective B212 haplotype.

Moreover, subjects that carried the B1B212 genotype showed later age of onset into CAD, lower blood pressure, lower triglycerides, higher HDL and lower CRP levels than subjects with other genotypes. (Table 14). Subjects carrying only the B212 allele showed the same traits. (Table 15). This shows that patients with CAD that have the B212 haplotype have a higher association with parameters predictive of lower risk of metabolic disorder and more severe cardiovascular disease.

TABLE 12

Table 12. Comparisons of Health Parameters between Control Patients with B212 and Patients without B212

| haplotype | | Age | | BMI | | BPS | | BPD | | TG | |
|---|---|---|---|---|---|---|---|---|---|---|---|
| B212 | N | mean | SD | mean | SD | mean | SD | mean | SD | mean | SD |
| No | 281 | 53.7 | 7.5 | 24.4 | 2.5 | 125.5 | 16.0 | 80.4 | 9.8 | 142.4 | 87.0 |
| Yes | 20 | 52.7 | 8.3 | 23.6 | 2.5 | 123.2 | 15.5 | 78.1 | 8.5 | 103.7 | 71.4 |
| p | | | | | | | | | | p = 0.04 | |

| haplotype | | TCHOL | | HDL | | LDL | | CRP | | Log CRP | | Fibrinogin | |
|---|---|---|---|---|---|---|---|---|---|---|---|---|---|
| B212 | N | mean | SD | mean | SD | mean | SD | mean | SD | mean | SD | mean | SD |
| No | 281 | 195.7 | 33.7 | 49.9 | 11.9 | 117.9 | 30.4 | 1.20 | 3.50 | −0.82 | 1.4 | 313.7 | 58.4 |
| Yes | 20 | 190.1 | 30.4 | 56.7 | 15.6 | 112.7 | 27.2 | 0.83 | 1.21 | −1.12 | 1.48 | 298.7 | 53.6 |
| p | | | | p = 0.01 | | | | | | | | | |

TABLE 13

Comparisons of Health Parameters between Control Patients with B212 and Patients without B212

| haplotype | | Age | | BMI | | BPS | | BPD | | TG | |
|---|---|---|---|---|---|---|---|---|---|---|---|
| B212 | N | mean | SD | mean | SD | mean | SD | mean | SD | mean | SD |
| No | 292 | 53.8 | 7.5 | 24.8 | 2.2 | 122.8 | 16.5 | 79.7 | 8.7 | 147.1 | 84.0 |
| Yes | 7 | 56.3 | 9.7 | 26.1 | 1.2 | 120.1 | 14.1 | 78.1 | 11.7 | 123.0 | 37.6 |
| p** | | | | | | p = 0.025 | | | | | |

| haplotype | | TCHOL | | HDL | | LDL | | CRP | | Log CRP | | Fibrinogin | |
|---|---|---|---|---|---|---|---|---|---|---|---|---|---|
| B212 | N | mean | SD | mean | SD | mean | SD | mean | SD | mean | SD | mean | SD |
| No | 281 | 176.6 | 37.9 | 43.9 | 11.0 | 103.3 | 32.5 | 2.20 | 4.43 | −0.03 | 1.17 | 335.9 | 69.5 |
| Yes | 20 | 193.7 | 71.9 | 52.4 | 23.4 | 116.7 | 66.8 | 0.68 | 0.50 | −0.62 | 0.74 | 309.4 | 57.5 |
| p | | | | | | | | | | p < 0.0001 | | | |

TABLE 14

Means and Standard Deviations of Key Health Parameters by Beta Promoter Genotype Pattern in CAD Patients.

| | | Age | | Age of Onset | | BMI | | BPS | | BPD | | TG | |
|---|---|---|---|---|---|---|---|---|---|---|---|---|---|
| Genotype | N | mean | SD | mean | SD | mean | SD | mean | SD | mean | SD | mean | SD |
| B1B1 | 53 | 54.9 | 7.4 | 51.9 | 7.5 | 24.7 | 2.6 | 121.3 | 17.2 | 78.7 | 9.3 | 138.9 | 83.8 |
| B1B2 | 120 | 53.0 | 7.5 | 49.2 | 7.3 | 24.6 | 2.2 | 123.6 | 15.7 | 80.3 | 9.0 | 155.8 | 92.8 |
| B1B212 | 7 | 56.3 | 9.7 | 52.7 | 8.1 | 26.1 | 1.2 | 120.1 | 14.1 | 78.1 | 11.7 | 123.0 | 37.6 |
| B1B3 | 9 | 55.4 | 10.0 | 52.6 | 8.9 | 25.1 | 1.6 | 125.4 | 16.8 | 80.1 | 9.0 | 140.0 | 66.1 |
| B1B4 | 23 | 54.8 | 6.5 | 50.7 | 7.8 | 25.1 | 1.6 | 122.6 | 17.8 | 80.1 | 8.4 | 168.0 | 91.6 |
| B2B2 | 48 | 53.0 | 7.5 | 48.5 | 7.5 | 24.2 | 2.3 | 120.3 | 17.0 | 78.2 | 7.2 | 142.5 | 77.6 |
| B2B3 | 14 | 55.5 | 8.3 | 51.4 | 9.8 | 25.3 | 2.1 | 122.9 | 15.5 | 79.6 | 9.0 | 123.9 | 49.1 |
| B2B4 | 19 | 52.5 | 6.2 | 47.5 | 6.5 | 26.1 | 1.9 | 125.3 | 20.4 | 81.6 | 10.0 | 128.5 | 65.0 |

| | | TCHOL | | HDL | | LDL | | CRP | | Log CRP | | Fibrinogin | |
|---|---|---|---|---|---|---|---|---|---|---|---|---|---|
| Genotype | N | mean | SD | mean | SD | mean | SD | mean | SD | mean | SD | mean | SD |
| B1B1 | 53 | 172.9 | 40.0 | 44.4 | 11.8 | 99.6 | 26.9 | 2.20 | 3.35 | 0.09 | 1.17 | 350.5 | 65.9 |
| B1B2 | 120 | 181.6 | 35.6 | 45.2 | 10.9 | 105.5 | 31.9 | 1.80 | 3.50 | −0.17 | 1.1 | 323.8 | 54.7 |
| B1B212 | 7 | 193.7 | 71.9 | 52.4 | 23.4 | 116.7 | 66.8 | 0.68 | 0.50 | −0.62 | 0.74 | 309.4 | 57.5 |
| B1B3 | 9 | 154.6 | 46.2 | 42.6 | 14.9 | 84.0 | 39.4 | 1.33 | 1.20 | −0.16 | 1.05 | 324.7 | 52.1 |
| B1B4 | 23 | 176.5 | 38.6 | 39.4 | 9.8 | 106.6 | 36.2 | 2.95 | 6.30 | 0.10 | 1.24 | 357.9 | 123.4 |
| B2B2 | 48 | 174.0 | 39.6 | 42.7 | 10.2 | 102.8 | 35.5 | 2.76 | 6.14 | 0.03 | 1.31 | 331.3 | 62.1 |
| B2B3 | 14 | 179.9 | 46.9 | 45.4 | 7.5 | 109.7 | 39.8 | 1.17 | 0.91 | −0.11 | 0.77 | 331.5 | 42.4 |
| B2B4 | 19 | 179.1 | 28.4 | 43.4 | 12.6 | 110.0 | 27.3 | 3.61 | 6.84 | 0.09 | 1.44 | 351.7 | 99.0 |

TABLE 15

Mean and Standard Deviations of Key Health Parameters by Patients Who Carried at Least 1 Beta Promoter Haplotype

| | | Age | | Age of Onset | | BMI | | BPS | | BPD | | TG | |
|---|---|---|---|---|---|---|---|---|---|---|---|---|---|
| Haplotype | N | mean | SD | mean | SD | mean | SD | mean | SD | mean | SD | mean | SD |
| B1 | 212 | 53.9 | 7.5 | 50.3 | 7.6 | 24.8 | 2.2 | 122.9 | 16.2 | 79.8 | 9.0 | 151.1 | 88.1 |
| B2 | 201 | 53.1 | 7.4 | 49.0 | 7.5 | 24.7 | 2.2 | 122.9 | 16.4 | 79.9 | 8.7 | 147.8 | 84.8 |
| B3 | 26 | 55.5 | 8.6 | 51.8 | 8.9 | 25.3 | 1.9 | 123.2 | 15.2 | 79.9 | 8.7 | 132.7 | 55.9 |
| B4 | 46 | 54.1 | 6.5 | 49.5 | 7.2 | 25.6 | 1.8 | 123.6 | 18.2 | 80.9 | 8.9 | 148.7 | 80.4 |
| B212 | 7 | 56.3 | 9.7 | 52.7 | 8.1 | 26.1 | 1.2 | 120.1 | 14.1 | 78.1 | 11.7 | 123.0 | 37.6 |

| | | TCHOL | | HDL | | LDL | | CRP | | Log CRP | | Fibrinogin | |
|---|---|---|---|---|---|---|---|---|---|---|---|---|---|
| Haplotype | N | mean | SD | mean | SD | mean | SD | mean | SD | mean | SD | mean | SD |
| B1 | 212 | 178.1 | 39.2 | 44.5 | 11.9 | 103.6 | 33.3 | 1.95 | 3.75 | −0.09 | 1.12 | 333.7 | 68.9 |
| B2 | 201 | 179.4 | 36.7 | 44.4 | 10.7 | 105.4 | 32.9 | 2.13 | 4.57 | −0.09 | 1.17 | 328.6 | 61.3 |
| B3 | 26 | 169.7 | 44.5 | 44.1 | 10.8 | 99.1 | 38.6 | 1.20 | 0.98 | −0.15 | 0.86 | 331.0 | 44.1 |
| B4 | 46 | 176.6 | 32.7 | 41.7 | 11.4 | 106.7 | 31.2 | 3.06 | 6.20 | 0.07 | 1.28 | 353.3 | 107.3 |
| B212 | 7 | 193.7 | 71.9 | 52.4 | 23.4 | 116.7 | 66.8 | 0.68 | 0.50 | −0.62 | 0.74 | 309.4 | 57.5 |

The results of these experiments suggest demonstrate that B212 haplotype is a protective factor in cardiovascular and metabolic disorders.

EQUIVALENTS AND INCORPORATION BY REFERENCE

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

The instant application includes numerous citations to learned texts, published articles and patent applications as well as issued U.S. and foreign patents. The entire contents of all of these citations are hereby incorporated by reference herein.

We claim:

1. A method for determining whether a human subject is likely to have or is predisposed to developing insulin resistance comprising obtaining a nucleic acid sample from said human subject and detecting a haplotype comprising allele 1 of IL-1B (−511), allele 2 of IL-1A (+4845) and allele 2 of IL-1B (+3954) in said sample, wherein a human subject who possesses the haplotype is more likely to have or is predisposed to developing insulin resistance when compared to a human subject who does not possess the haplotype.

2. The method of claim 1, wherein the insulin resistance is associated with type 2 diabetes or metabolic syndrome.

3. A method for determining whether a human subject is likely to have or is predisposed to expressing a decreased level of C-reactive protein comprising obtaining a nucleic acid sample from said human subject and detecting in said sample a B212 haplotype, wherein the B212 haplotype comprises allele 2 of IL-1B (−511), allele 1 of IL-1B (−1464) and allele 2 of IL-1B (−3737), wherein a human subject who possesses the B212 haplotype is likely to have or is predisposed to expressing a decreased level of C-reactive protein when compared to a human subject who does not possess the B212 haplotype.

4. The method of claim 3, wherein the human subject is Asian or of Asian descent.

5. The method of claim 3, wherein the human subject is Korean or of Korean descent.

6. The method of claim 3, wherein the human subject who possesses the B212 haplotype is likely to have or is predisposed to expressing an increased level of high density lipoprotein when compared to a human subject who does not possess the B212 haplotype.

7. The method of claim 3, wherein the human subject who possesses the B212 haplotype is likely to have or is predisposed to expressing a decreased level of low density lipoprotein when compared to a human subject who does not possess the B212 haplotype.

8. The method of claim 3, wherein the human subject who possesses the B212 haplotype is likely to have or is predisposed to expressing a decreased level of triglyceride when compared to a human subject who does not possess the B212 haplotype.

9. The method of claim 3, wherein the human subject who possesses the B212 haplotype is likely to have or is predisposed to a decreased risk of cardiovascular disorders or metabolic disorders when compared to a human subject who does not possess the B212 haplotype.

* * * * *